US012807920B2

(12) United States Patent
Hori

(10) Patent No.: US 12,807,920 B2
(45) Date of Patent: Nov. 24, 2026

(54) CONTINUOUS PRODUCTION METHOD OF MICROORGANISMS THAT DO NOT REQUIRE STERILIZATION AND SYSTEM THEREFOR

(71) Applicant: National University Corporation Tokai National Higher Education and Research System, Aichi (JP)

(72) Inventor: Katsutoshi Hori, Aichi (JP)

(73) Assignee: National University Corporation Tokai National Higher Education and Research System, Aichi (JP)

( * ) Notice: Subject to any disclaimer, the term of this patent is extended or adjusted under 35 U.S.C. 154(b) by 480 days.

(21) Appl. No.: 18/255,865

(22) PCT Filed: Dec. 6, 2021

(86) PCT No.: PCT/JP2021/044787
§ 371 (c)(1),
(2) Date: Jun. 3, 2023

(87) PCT Pub. No.: WO2022/118987
PCT Pub. Date: Jun. 9, 2022

(65) Prior Publication Data

US 2024/0101955 A1 Mar. 28, 2024

(30) Foreign Application Priority Data

Dec. 4, 2020 (JP) ................................ 2020-202253

(51) Int. Cl.
*C12N 1/20* (2026.01)
*C12M 1/00* (2006.01)
*C12M 1/34* (2006.01)
*C12N 1/16* (2026.01)

(52) U.S. Cl.
CPC .............. *C12N 1/20* (2013.01); *C12M 29/00* (2013.01); *C12M 41/30* (2013.01); *C12N 1/16* (2013.01)

(58) Field of Classification Search
CPC ........................................................ C12N 1/20
See application file for complete search history.

(56) References Cited

U.S. PATENT DOCUMENTS

| | | | | | |
|---|---|---|---|---|---|
| 3,898,959 | A * | 8/1975 | Chen | C12N 1/38 435/938 |
| 5,624,841 | A * | 4/1997 | Raven | C12N 1/20 435/244 |
| 2015/0024470 | A1 | 1/2015 | Hori | |
| 2020/0131543 | A1 | 4/2020 | Aurich | |
| 2021/0130207 | A1 | 5/2021 | Fujioka | |
| 2021/0276904 | A1 | 9/2021 | Hori | |

FOREIGN PATENT DOCUMENTS

| | | | |
|---|---|---|---|
| CN | 111378254 | A | 7/2020 |
| EP | 3712247 | A1 | 9/2020 |
| JP | 1157762 | A | 3/1999 |
| JP | 2002126785 | A | 5/2002 |
| JP | 2003274937 | A | 9/2003 |
| JP | 2010227858 | A | 10/2010 |
| JP | 2013527023 | | 6/2013 |
| JP | 2020505024 | | 2/2020 |
| WO | 2011100089 | A2 | 8/2011 |
| WO | 2013108775 | A1 | 7/2013 |
| WO | 2018130674 | A2 | 7/2018 |
| WO | 2018207825 | | 11/2018 |
| WO | 2019098255 | | 5/2019 |
| WO | 2020009232 | A1 | 1/2020 |

OTHER PUBLICATIONS

Google translation of JP3065348 B2 (Year: 2000).*
International Search Report for related International Application No. PCT/JP2021/044787 mailed Feb. 1, 2022 and its English Translation.
First Office Action for corresponding Japanese Application No. 2021-068159 mailed Jun. 24, 2021 and its English Machine Translation.
Bhalerao A. et al.; "Continuous cultivation strategy for yeast industrial wastewater-based polyhydroxyalkanoate production", Journal of Bioscience and Bioengineering, vol. 129, No. 5, Dec 10, 2019, pp. 595-602.
Chitnis A. V. et al.; "Non-sterile cultivation of oleaginous organisms", Trends in Biotechnology, May 3, 2024, pp. 1-5.
Extended European Search Report (EESR), including the supplementary European search report and the European search opinion for corresponding European Application No. 21900730.9 dated Dec. 2, 2024.
Teng Li et al.; "Open and continuous fermentation: Products, conditions and bioprocess economy", Biotechnology Journal, vol. 9, No. 12, Dec 5, 2014, pp. 1503-1511.
Communication pursuant to Article 94(3) EPC in counterpart European Application No. 21900730.9 dated Jul. 28, 2026.
Elbing Karen L. et al., "Recipes and Tools for Culture of *Escherichia coli*", Current Protocols in Molecular Biology, vol. 125, art. No. e83, Nov. 9, 2018 (Nov. 9, 2018), pp. 1-19, XP093419103, DOI: 10.1002/cpmb.83.
Nelson S. M.: "The effect of temperature on viability of carbon- and nitrogen-starved *Escherichia coli*", Microbial Ecology, vol. 32, Jul. 1, 1996 (Jul. 1, 1996), pp. 11-21, XP093418968.

* cited by examiner

*Primary Examiner* — Brian Gangle
*Assistant Examiner* — Lakia J Jackson-Tongue
(74) *Attorney, Agent, or Firm* — Renner, Otto, Boisselle & Sklar, LLP

(57) ABSTRACT

The objective of the present invention is to provide a method and a system for continuous production of microorganisms without the need for sterilization. The present invention provides a novel method for continuously producing microorganisms by proliferating a stored microorganism inoculum without the need for sterilization and a system therefor. According to the present invention, a novel method and system for producing microorganisms in which the need for sterilization for avoiding contamination with unwanted bacteria is reduced as compared with general methods and systems for producing microorganisms are provided.

20 Claims, 7 Drawing Sheets

No. 3 and No. 4 are the same as Fig 2. No. 5 is diluted 10-fold with an inorganic salt medium free of a carbon source

CONTINUOUS PRODUCTION METHOD OF MICROORGANISMS THAT DO NOT REQUIRE STERILIZATION AND SYSTEM THEREFOR

This application is a national phase of International Application No. PCT/JP2021/044787 filed Dec. 6, 2021, which claims priority to Japan Application No. 2020-202253 filed Dec. 4, 2020, the entireties of which are hereby incorporated by reference.

TECHNICAL FIELD

The present invention is directed to a novel method of manufacturing microorganisms and a system therefor.

BACKGROUND ART

Microorganisms have been used in wide-ranging applications, such as production of useful substances, food production, water treatment, and decomposition of specific substances such as oil and fat. Generally, methods of growing microorganisms for such applications are roughly categorized into batch culture, fed batch culture, and continuous culture. At an industrial scale, formulations and products comprising a large quantity of microorganisms are primarily manufactured through batch culture or fed batch culture, which retrieves a culture solution for each cycle of culture. Efficient large-scale manufacture of microorganisms through continuous culture is challenging and is thus hardly practiced. In general, media and manufacturing apparatuses are sterilized in culturing of microorganisms, whether batch culture, fed batch culture, or continuous culture, in order to prevent infiltration of microorganisms other than the microorganisms of interest or germ pollution. Sterilization is essential, especially in continuous culture, due to an elevated risk of growth of infiltrated microorganisms or bacteriophages during long-term culture. However, even with sterilization, there is a possibility of growth of heat resistant microorganisms that could not be completely sterilized or bacteriophages that readily infiltrate during long-term operation of continuous culture. Continuous culture has been avoided in view of the magnitude of damage in case of such growth of germs, etc., and challenges in quality control for manufactured products. Meanwhile, minor infiltration of germs, etc. would be tolerable for microorganism formulations, etc. used in wastewater treatment, etc., if growth of microorganisms of interest or the potency thereof is not affected. However, even in such a case, it is obvious that infiltration by germs, etc. needs to be suppressed as much as possible in terms of quality control of products, so that media and manufacturing apparatuses have been sterilized as much as possible. If sterilization is difficult, short-term batch culture can be conducted as an exception so that infiltrated germs, etc. would not grow and affect the growth or performance of microorganisms of interest.

As one example, an automatic microorganism feeder, which refrigerates seed microorganisms, feeds the microorganisms to a growth vessel periodically such as once daily, and grows the seed microorganisms to manufacture a microorganism formulation, and feeds the microorganism formulation manufactured in this manner into oil and fat-containing wastewater, has been developed in order to treat the oil and fat-containing wastewater (Patent Literature 1). Meanwhile, microorganism formulations used in such a case are also generally manufactured by batch culture.

CITATION LIST

Patent Literature

[1] International Publication No. WO 2018/207825

SUMMARY OF INVENTION

Solution to Problem

The present invention provides a novel manufacturing method for continuously growing a large quantity of microorganisms and a system therefor. The present invention can provide a method of continuously growing microorganisms with reduced need for sterilization as compared to conventional methods, i.e., method of manufacturing microorganisms. The continuous manufacturing method of the invention can economize the amount of microorganisms used as spawns and can efficiently manufacture a large quantity of microorganisms.

The present invention provides the following.

(Item 1)

A method of feeding a microorganism formulation in the treatment of oil and fat-containing wastewater, characterized by:

- continuously supplying a medium at constant flow rate Y (L/h) and a carbon source at constant flow rate Q (L/h) to a thermostatic vessel for 20 hours or longer;
- growing oil and fat degrading microorganisms in a culture solution in the thermostatic vessel by aerating the thermostatic vessel to manufacture a microorganism formulation; and
- continuously discharging the microorganism formulation comprising a substantially constant concentration of microorganisms from the thermostatic vessel at constant flow rate F (L/h) and feeding the discharged microorganism formulation to the oil and fat-containing wastewater at constant flow rate F for 20 hours or longer.

(Item 2)

The method of item 1, characterized in that:

- the culture solution has a medium component at a concentration of interest, and the medium fed at constant flow rate Y is produced with a concentrated medium having a medium component at a concentration of about 10-fold or greater than the medium component at the concentration of interest, supplied at constant flow rate Y1 (L/h), and water supplied independently from the concentrated medium at constant flow rate Y2 (L/h), wherein Y1+Y2=Y; and
- (1) the concentrated medium and the water are supplied separately to the thermostatic vessel to be a medium component with the concentration of interest in the thermostatic vessel, or
- (2) the concentrated medium and the water are mixed in a mixing vessel or a supply line to produce a mixture having a medium component at the concentration of interest, and the mixture is continuously supplied to the thermostatic vessel.

(Item 3)

The method of item 1 or 2, characterized in that the carbon source is supplied to the thermostatic vessel so that a carbon source concentration of a culture solution in the thermostatic vessel would always be about 0.01 w/v % or less.

(Item 4)

The method of any one of items 1 to 3, characterized in that the thermostatic vessel is operated so that a temperature of a culture solution in the thermostatic vessel would be 20 to 35° C., a dissolved oxygen concentration would be 0.1 mg/L or greater, and a pH would be 6.0 to 8.0.

(Item 5)

The method of any one of items 1 to 4, characterized in that a microorganism formulation continuously discharged from the thermostatic vessel comprises the oil and fat-degrading microorganisms at $1\times10^9$ cells/mL or greater.

(Item 6)

The method of any one of items 1 to 5, characterized in that medium volume Y (L) supplied each hour to the thermostatic vessel is a volume that is 1/30 to ½ of volume V (L) of a culture solution in the thermostatic vessel.

(Item 7)

The method of item 6, characterized in that medium volume Y (L) supplied each hour to the thermostatic vessel is a volume that is 1/12 to ½ of volume V (L) of a culture solution in the thermostatic vessel.

(Item 8)

The method of any one of items 1 to 7, characterized in that Y is equal to F.

(Item 9)

The method of any one of items 1 to 7, characterized in that:

(i) a suspension of spawns of oil and fat degrading microorganisms with a concentration of $1\times10^8$ to $2\times10^{10}$ cells/mL is continuously supplied to the thermostatic vessel at constant flow rate X (L/h) for 20 hours or longer, wherein X≤Y/100 and (X+Y) is equal to F; or (ii) spawns are stored as dry cells of oil and fat degrading microorganisms, and a spawn suspension prepared to have a concentration of $k\times2\times10^{10}$ cells/mL or greater (k≥1) prior to being supplied to the thermostatic vessel is continuously supplied to the thermostatic vessel at constant flow rate Z (L/h) for 20 hours or longer, wherein Z=X/k and (Z+Y) is equal to F.

(Item 10)

The method of item 9, characterized in that the spawns in (i) are prepared by removing culture supernatant from batch-cultured oil and fat degrading microorganisms, resuspending the microorganisms in a fresh medium free of a carbon source so that a concentration would be $1\times10^8$ to $2\times10^{10}$ cells/mL, and refrigerating the microorganisms.

(Item 11)

The method of item 9, characterized in that the spawns in (i) are stored as dry cells of oil and fat degrading microorganisms and suspended in a liquid so that a concentration would be $1\times10^8$ to $2\times10^{10}$ cells/mL prior to being supplied to the thermostatic vessel as a spawn suspension, and a spawn suspension prepared in this manner is continuously supplied to the thermostatic vessel.

(Item 12)

The method of any one of items 1 to 8, characterized in that spawns of oil and fat degrading microorganisms stored as dry cells are directly supplied to the thermostatic vessel so that a microorganism concentration would be $1\times10^8$ cells/mL.

(Item 13)

The method of item 9, 11, or 12, wherein the dry cells are stored at ambient temperature.

(Item 14)

The method of any one of items 9 and 11 to 13, characterized in that the dry cells are dry cells manufactured by a step of mixing whey with the oil and fat degrading microorganisms and drying a resulting mixture under reduced pressure.

(Item 15)

The method of any one of items 1 to 14, characterized in that:

two thermostatic vessels are provided, wherein the method comprises the step of:

(1) discharging the entire culture solution in one of the two thermostatic vessels every 1 to 7 days at a timing in accordance with a predetermined condition, then resupplying a medium at a volume of 95 to 99% of the discharged culture solution to the thermostatic vessel, further supplying a spawn suspension of oil and fat degrading microorganisms with a concentration of $1\times10^8$ to $1\times10^{10}$ cells/mL to the thermostatic vessel so that a volume would be 5 to 1% of a discharged culture solution, and aerating a resulting suspension for 12 to 24 hours to amplify the oil and fat degrading microorganisms in the thermostatic vessel for a moment; or (2) discharging the entire culture solution in one of the two thermostatic vessels every 1 to 7 days at a timing in accordance with a predetermined condition, then resupplying a medium of the same volume as the discharged culture solution to the thermostatic vessel, further supplying dry cells of spawns of the oil and fat degrading microorganisms so that an oil and fat degrading microorganism concentration in the thermostatic vessel would be $1\times10^6$ to $1\times10^8$ cells/mL, and aerating a resulting suspension for 12 to 24 hours to amplify the oil and fat degrading microorganisms in the thermostatic vessel for a moment.

(Item 16)

The method of any one of items 1 to 15, characterized in that the oil and fat degrading microorganisms comprise at least one type selected from the group consisting of bacteria and yeasts.

(Item 17)

The method of any one of items 1 to 16, characterized in that the oil and fat degrading microorganisms comprise at least one type selected from the group consisting of gram-negative bacteria and yeasts.

(Item 18)

The method of any one of items 1 to 17, characterized in that the oil and fat degrading microorganisms comprise at least one type selected from the group consisting of bacteria of the genus *Burkholderia* and yeasts of the genus *Yarrowia.*

(Item 19)

A method of treating the oil and fat-containing wastewater, comprising the method of any one of items 1 to 18.

(Item 20)

A system for supplying an oil and fat degrading microorganism formulation to oil and fat-containing wastewater for the method of any one of items 1 to 18 or the method of claim 19, comprising:

a thermostatic vessel;

a blower for aerating the thermostatic vessel;

a medium storage vessel;

a medium supplying unit, comprising a first pump, for continuously supplying a medium from the medium storage vessel to the thermostatic vessel at constant flow rate Y (L/h);

a carbon source storage vessel;

a carbon source supplying unit, comprising a second pump, for continuously supplying a carbon source to the thermostatic vessel at constant flow rate Q (L/h); and discharging means configured to discharge a microorganism formulation from the thermostatic vessel at constant flow rate F (L/h) and to feed the microorganism formulation into the oil and fat-containing wastewater.

(Item 21)

The system of item 20, characterized in that the medium supplying unit comprises a water supplying system for supplying water at constant flow rate Y2 (L/h) in addition to the first pump for continuously supplying a medium from the medium storage vessel to the thermostatic vessel at constant flow rate Y1 (L/h), wherein Y1+Y2=Y.

(Item 22)

The system of item 20 or 21, characterized by further comprising:

- a spawn storage unit for storing a spawn suspension of the oil and fat-degrading microorganisms;
- a cooling system for cooling the spawn storage unit; and
- a third pump configured to continuously supply the spawn suspension from the spawn storage unit to the thermostatic vessel at constant flow rate X (L/h).

(Item 23)

The system of item 20 or 21, further comprising:

- a spawn storage unit for storing spawns of the oil and fat-degrading microorganisms as dry cells;
- a spawn suspension preparation vessel for preparing a spawn suspension so that a concentration of the spawns would be $1\times10^8$ to $2\times10^{10}$ cells/mL;
- dry cell supplying means configured to supply the dry cells from the spawn storage unit to the spawn suspension preparation vessel; and
- a fourth pump configured to continuously supply the spawn suspension from the spawn suspension preparation vessel to the thermostatic vessel at constant flow rate X (L/h).

(Item 24)

The system of item 20 or 21, characterized by further comprising:

- a spawn storage unit for storing spawns of the oil and fat-degrading microorganisms as dry cells; and
- dry cell supplying means configured to supply the dry cells from the spawn storage unit to the thermostatic vessel at $1\times10^8$ cells or less of spawns per 1 mL of thermostatic vessel.

(Item 25)

The system of any one of items 22 to 24, characterized in that the spawn storage unit does not comprise a blower.

(Item 26)

A method of manufacturing an oil and fat degrading microorganism formulation, comprising:

- batch-culturing oil and fat degrading microorganisms;
- removing culture supernatant of the batch-cultured culture solution to obtain a wet cell clump of the grown oil and fat degrading microorganisms; and
- resuspending the wet cell clump in a fresh medium so that a concentration would be $1\times10^8$ to $2\times10^{10}$ cells/mL.

(Item 27)

The method of item 26, wherein the fresh medium is an inorganic salt medium free of a carbon source.

(Item 28)

The method of item 26 or 27, wherein the method comprises resuspending the wet cell clump in the fresh medium so that a concentration would be $1\times10^8$ to $9\times10^9$ cells/mL.

(Item 29) An oil and fat degrading microorganism formulation manufactured by the method of any one of items 26 to 28.

(Item 30)

A method of manufacturing a dry microorganism formulation, comprising mixing whey with microorganisms and drying a resulting mixture under reduced pressure.

(Item 31)

The method of item 30, wherein the microorganisms comprise gram-negative bacteria, which are non-spore-forming bacteria.

(Item 32)

A protective agent for drying microorganisms under reduced pressure, having whey as an active ingredient.

(Item 33)

The protective agent of item 32, wherein the microorganisms comprise gram-negative bacteria, which are non-spore-forming bacteria.

(Item 34)

A dry microorganism formulation comprising gram-negative bacteria, which are non-spore-forming bacteria, and whey.

(Item 35)

A method of feeding a microorganism formulation comprising oil and fat degrading microorganism in the treatment of oil and fat-containing wastewater, comprising a procedure comprising the steps of:

- step 1: continuously feeding a first microorganism formulation stored in a reservoir to the oil and fat-containing wastewater;
- step 2: feeding a second microorganism formulation from a thermostatic vessel to the reservoir when it is detected that an amount of the first microorganism formulation has decreased to a threshold value in the reservoir;
- step 3: starting to supply water to the thermostatic vessel when it is detected that an amount of the second microorganism formulation has decreased to a threshold value in the thermostatic vessel;
- step 4: supplying a certain amount of a concentrated medium, a carbon source, and spawns of the oil and fat degrading microorganisms to the thermostatic vessel when it is detected that a water level has been elevated to a threshold value due to supplying water to the thermostatic vessel; and
- step 5: growing the spawns in the culture solution to manufacture a third microorganism formulation in the thermostatic vessel;
  - wherein the method is characterized by further repeating the procedure, and the second microorganism formulation and third microorganism formulation of a preceding procedure are the first microorganism formulation and second microorganism formulation in a subsequent procedure, respectively, and
  - wherein each of the first microorganism formulation, the second microorganism formulation, and the third microorganism formulation comprises the oil and fat degrading microorganisms.

(Item 36)

The method of item 35, comprising the following step 3-1 and/or step 3-2 between step 3 and step 4:

- step 3-1: draining again after detecting that a predetermined amount of water has been supplied to the thermostatic vessel, resupplying water after detecting that a water level has decreased to a threshold value, and repeating the draining and supplying of water any number of times to wash the inside of the thermostatic vessel; and
- step 3-2: aerating water in the thermostatic vessel for a certain period of time for dechlorination.

(Item 37)

The method of item 35 or 36, wherein each of the first microorganism formulation, the second microorganism formulation, and the third microorganism formulation comprises the oil and fat degrading microorganisms at $1\times10^9$ cells/mL.

(Item 38)

The method of any one of items 35 to 37, characterized in that the carbon source is supplied to the thermostatic vessel so that a carbon source concentration in a microorganism formulation discharged from the thermostatic vessel would be about 0.01 w/v % or less.

(Item 39)

The method of any one of items 35 to 38, characterized in that a thermostatic vessel is operated so that a temperature of a culture solution in the thermostatic vessel would be 20 to 35° C., a dissolved oxygen concentration would be 0.1 mg/L or greater, and a pH would be 6.0 to 8.0.

(Item 40)

The method of any one of items 35 to 39, characterized in that the spawns are prepared by removing culture supernatant from batch-cultured oil and fat degrading microorganisms, resuspending the microorganisms in a fresh medium free of a carbon source so that a concentration would be $1\times10^8$ to $2\times10^{10}$ cells/mL, and refrigerating the microorganisms.

(Item 41)

The method of any one of items 35 to 39, characterized in that the spawns are stored as dry cells of the oil and fat degrading microorganisms and suspended in a liquid so that a concentration would be $1\times10^8$ to $2\times10^{10}$ cells/mL prior to being supplied to the thermostatic vessel as a spawn suspension, and a spawn suspension prepared in this manner is supplied to the thermostatic vessel.

(Item 42)

The method of any one of items 35 to 39, characterized in that spawns of oil and fat degrading microorganisms stored as dry cells are directly supplied to the thermostatic vessel so that a microorganism concentration would be $1\times10^8$ cells/mL.

(Item 43)

The method of item 41 or 42, wherein the dry cells are stored at ambient temperature.

(Item 44)

The method of any one of items 41 to 43, characterized in that the dry cells are dry cells manufactured by a step of mixing whey with the oil and fat degrading microorganisms and drying a resulting mixture under reduced pressure.

(Item 45)

The method of any one of items 35 to 44, characterized in that an amount of a microorganism formulation in the reservoir and/or thermostatic vessel is detected by a water level gauge or a liquid level sensor.

(Item 46)

The method of any one of items 35 to 45, characterized in that the oil and fat degrading microorganisms comprise at least one type selected from the group consisting of bacteria and yeasts.

(Item 47)

The method of any one of items 35 to 46, characterized in that the oil and fat degrading microorganisms comprise at least one type selected from the group consisting of gram-negative bacteria and yeasts.

(Item 48)

The method of any one of items 35 to 47, characterized in that the oil and fat degrading microorganisms comprise at least one type selected from the group consisting of bacteria of the genus *Burkholderia* and yeasts of the genus *Yarrowia*.

(Item 49)

A method of treating the oil and fat-containing wastewater, comprising the method of any one of items 35 to 48.

(Item 50)

A system for supplying an oil and fat degrading microorganism formulation to oil and fat-containing wastewater for the method of any one of items 35 to 48 or the method of Item 49, comprising:

- a thermostatic vessel comprising a mechanism for detecting an amount of contents in a vessel;
- a blower for aerating the thermostatic vessel;
- a reservoir comprising a mechanism for detecting an amount of contents in a vessel for continuously supplying a microorganism formulation manufactured in the thermostatic vessel to the oil and fat-containing wastewater while storing the microorganism formulation;
- a medium storage vessel;
- a medium supplying unit comprising the following (1) and (2)
  - (1) first controlling means and a first pump for supplying a concentrated medium from the medium storage vessel to the thermostatic vessel, and
  - (2) water supply controlling means that operates in conjunction with the mechanism for detecting an amount of contents in the thermostatic vessel;
- a carbon source storage vessel;
- a carbon source supplying unit comprising second controlling means and a second pump for supplying a carbon source from the carbon source storage vessel to the thermostatic vessel;
- first discharging means configured to continuously discharge a microorganism formulation from the reservoir and to feed the microorganism formulation into the oil and fat-containing wastewater;
- second discharging means configured to discharge a microorganism formulation from the thermostatic vessel by operating in conjunction with the mechanism for detecting an amount of contents in the reservoir and to feed the microorganism formulation into the reservoir;
- a spawn storage unit for storing a spawn suspension of the oil and fat degrading microorganisms;
- a cooling system for cooling the spawn storage unit; and
- third controlling means and a third pump configured to supply the spawn suspension from the spawn storage unit to the thermostatic vessel;
- characterized in that each of the first controlling means, the second controlling means, and the third controlling means operates in conjunction with the mechanism for detecting an amount of contents in the thermostatic vessel.

(Item 51)

The system of item 50, characterized in that the spawn storage unit does not comprise a blower.

(Item 52)

A system for supplying an oil and fat degrading microorganism formulation to oil and fat-containing wastewater for the method of any one of items 35 to 48 or the method of Item 49, comprising:

- a thermostatic vessel comprising a mechanism for detecting an amount of contents in a vessel;
- a blower for aerating the thermostatic vessel;
- a reservoir comprising a mechanism for detecting an amount of contents in a vessel for continuously supplying a microorganism formulation manufactured in the thermostatic vessel to the oil and fat-containing wastewater while storing the microorganism formulation;

a medium storage vessel;

a medium supplying unit comprising the following (1) and (2)

(1) first controlling means and a first pump for supplying a concentrated medium from the medium storage vessel to the thermostatic vessel, and (2) water supply controlling means that operates in conjunction with the mechanism for detecting an amount of contents in the thermostatic vessel;

a carbon source storage vessel;

a carbon source supplying unit comprising second controlling means and a second pump for supplying a carbon source from the carbon source storage vessel to the thermostatic vessel;

first discharging means configured to continuously discharge a microorganism formulation from the reservoir and to feed the microorganism formulation into the oil and fat-containing wastewater;

second discharging means configured to discharge a microorganism formulation from the thermostatic vessel by operating in conjunction with the mechanism for detecting an amount of contents in the reservoir and to feed the microorganism formulation into the reservoir;

a spawn storage unit for storing spawns of the oil and fat degrading microorganisms as dry cells;

a spawn suspension preparation vessel comprising spawn suspension preparation vessel water supply controlling means for preparing a spawn suspension so that a concentration of the spawns would be $1\times10^8$ to $2\times10^{10}$ cells/mL;

dry cell supply controlling means configured to supply the dry cells from the spawn storage unit to the spawn suspension preparation vessel at a controlled timing; and fourth controlling means and a fourth pump configured to supply the spawn suspension from the spawn suspension preparation vessel to the thermostatic vessel;

characterized in that each of the first controlling means, the second controlling means, and the fourth controlling means operates in conjunction with the mechanism for detecting an amount of contents in the thermostatic vessel.

(Item 53)

A system for supplying an oil and fat degrading microorganism formulation to oil and fat-containing wastewater for the method of any one of items 35 to 48 or the method of Item 49, comprising:

a thermostatic vessel comprising a mechanism for detecting an amount of contents in a vessel;

a blower for aerating the thermostatic vessel;

a reservoir comprising a mechanism for detecting an amount of contents in a vessel for continuously supplying a microorganism formulation manufactured in the thermostatic vessel to the oil and fat-containing wastewater while storing the microorganism formulation;

a medium storage vessel;

a medium supplying unit comprising the following (1) and (2)

(1) first controlling means and a first pump for supplying a concentrated medium from the medium storage vessel to the thermostatic vessel, and (2) water supply controlling means that operates in conjunction with the mechanism for detecting an amount of contents in the thermostatic vessel;

a carbon source storage vessel;

a carbon source supplying unit comprising second controlling means and a second pump for supplying a carbon source from the carbon source storage vessel to the thermostatic vessel;

first discharging means configured to continuously discharge a microorganism formulation from the reservoir and to feed the microorganism formulation into the oil and fat-containing wastewater;

second discharging means configured to discharge a microorganism formulation from the thermostatic vessel by operating in conjunction with the mechanism for detecting an amount of contents in the reservoir and to feed the microorganism formulation into the reservoir;

a spawn storage unit for storing spawns of the oil and fat degrading microorganisms as dry cells; and fifth controlling means and dry cell supplying means configured to supply the dry cells from the spawn storage unit to the thermostatic vessel at $1\times10^8$ cells or less of spawns per 1 mL of thermostatic vessel;

characterized in that each of the first controlling means, the second controlling means, and the fifth controlling means operates in conjunction with the mechanism for detecting an amount of contents in the thermostatic vessel.

(Item 54)

The system of any one of items 50 to 53, wherein the reservoir comprises an insulating material, thermal insulation coating, and/or a heating/cooling function.

(Item 55)

The system of any one of items 50 to 54, further comprising a blower or mechanical agitation means for agitating contents of the reservoir.

(Item A1)

A method of manufacturing a microorganism formulation, comprising:

batch-culturing microorganisms;

removing culture supernatant of the batch-cultured culture solution to obtain a wet cell clump of the grown microorganisms; and resuspending the wet cell clump in a fresh medium so that a concentration would be $1\times10^8$ to $2\times10^{10}$ cells/mL.

(Item A2)

The method of item A1, wherein the fresh medium is an inorganic salt medium free of a carbon source.

(Item A3)

The method of item A1 or A2, wherein the method comprises resuspending the wet cell clump in the fresh medium so that a concentration would be $1\times10^8$ to $9\times10^9$ cells/mL.

(Item A4)

A microorganism formulation manufactured by the method of any one of items A1 to A3.

(Item A5)

A method of manufacturing a dry microorganism formulation, comprising mixing whey with microorganisms and drying a resulting mixture under reduced pressure.

(Item A6)

The method of item A5, wherein the microorganisms comprise gram-negative bacteria, which are non-spore-forming bacteria.

(Item A7)

A protective agent for drying microorganisms under reduced pressure, having whey as an active ingredient.

(Item A8)

The protective agent of item A7, wherein the microorganisms comprise gram-negative bacteria, which are non-spore-forming bacteria.

(Item A9)

A dry microorganism formulation comprising gram-negative bacteria, which are non-spore-forming bacteria, and whey.

(Item B1)

A method of continuously manufacturing microorganisms, comprising:

continuously supplying, for 20 hours or longer, a first concentrated partial medium from a first medium storage vessel at constant flow rate Y1 (L/h), a second concentrated partial medium from a second medium storage vessel at flow rate Q (L/h), and water at constant flow rate Y2 (L/h), each independently to a thermostatic vessel, or to the thermostatic vessel after mixing in a mixing vessel or a supply line;

growing microorganisms that can assimilate a carbon source and grow in a culture solution in the thermostatic vessel by aerating the thermostatic vessel to continuously manufacture a microorganism culture solution for 20 hours or longer; and continuously discharging the microorganism culture solution comprising a substantially constant concentration of microorganisms from the thermostatic vessel at constant flow rate F (L/h) for 20 hours or longer;

characterized in that a medium required for the microorganisms is formed by a first medium component contained in the first concentrated partial medium, a second medium component contained in the second concentrated partial medium, and water.

(Item B2)

The method of item B1, characterized in that volume F (L) of the microorganism culture solution discharged each hour from the thermostatic vessel is a volume that is $\frac{1}{30}$ to $\frac{1}{2}$ of volume V (L) of a culture solution in the thermostatic vessel.

(Item B3)

The method of item B1 or B2, characterized in that the first concentrated partial medium or the second concentrated partial medium comprises a carbon source, and the concentrated partial medium comprising the carbon source is supplied to the thermostatic vessel so that a carbon source concentration of a culture solution in the thermostatic vessel would always be about 0.01 w/v % or less.

(Item B4)

The method of any one of items B1 to B3, characterized in that a flow rate of a fluid supplied to the thermostatic vessel other than the second concentrated partial medium is equal to a flow rate of the culture solution discharged from the thermostatic vessel.

(Item B5)

The method of any one of items B1 to B4, characterized in that a suspension of spawns of microorganisms is continuously supplied to the thermostatic vessel at constant flow rate X (L/h) for 20 hours or longer.

(Item B6)

The method of any one of items B1 to B5, wherein the method is performed by providing two thermostatic vessels and comprises before or after the continuous manufacture for 20 hours or longer, discharging the entire culture solution in one of the two thermostatic vessels every 1 to 30 days at a timing in accordance with a predetermined condition, then resupplying a first concentrated partial medium, a second concentrated partial medium, and water to the thermostatic vessel, further supplying spawns of the microorganisms to the thermostatic vessel, and aerating a resulting mixture for a certain period of time.

(Item B7)

The method of item B6, wherein one or both of the following steps are performed after discharging the culture solution in the thermostatic vessel and before supplying spawns of the microorganisms:

(1) an operation to supply and drain water one or more times before supplying a concentrated partial medium to wash a thermostatic vessel; and (2) an operation to aerate for a while after supplying water to eliminate chlorine in water.

(Item B8)

A method of continuously manufacturing microorganisms for growing microorganisms and continuously manufacturing a microorganism culture solution with a substantially constant concentration for 20 hours or longer at a substantially constant flow rate, comprising a procedure comprising the steps of:

step 1: continuously discharging a first microorganism-containing culture solution stored in a reservoir;

step 2: feeding a second microorganism-containing culture solution from a thermostatic vessel to the reservoir when it is detected that an amount of the first microorganism-containing culture solution has decreased to a threshold value in the reservoir;

step 3: starting to supply water to the thermostatic vessel when it is detected that an amount of the second microorganism-containing culture solution has decreased to a threshold value in the thermostatic vessel;

step 4: supplying a first concentrated partial medium from a first medium storage vessel, a second concentrated partial medium from a second medium storage vessel, and spawns of the microorganisms from a spawn storage vessel to the thermostatic vessel when it is detected that a water level has been elevated to a threshold value due to supplying water to the thermostatic vessel; and step 5: growing the spawns in the medium to manufacture a third microorganism-containing culture solution in the thermostatic vessel;

wherein the method is characterized by further repeating the procedure, and the second microorganism-containing culture solution and third microorganism-containing culture solution of a preceding procedure are the first microorganism-containing culture solution and second microorganism-containing culture solution in a subsequent procedure, respectively, and wherein each of the first microorganism-containing culture solution, the second microorganism-containing culture solution, and the third microorganism-containing culture solution comprises the microorganisms.

(Item B9)

The method of item B8, comprising the following step 3-1 and/or step 3-2 between step 3 and step 4:

step 3-1: draining water again after detecting that a predetermined amount of water has been supplied to the thermostatic vessel, resupplying water after detecting that a water level has decreased to a threshold value, and repeating the draining and supplying of water any number of times to wash the inside of the thermostatic vessel; and step 3-2: aerating water in the thermostatic vessel for a certain period of time for dechlorination.

(Item B10)

The method of item B8 or B9, characterized in that an amount of a culture solution in the reservoir and/or thermostatic vessel is detected by a water level gauge or a liquid level sensor.

(Item B11)

The method of any one of items B1 to B10, wherein one of the first concentrated partial medium and the second concentrated partial medium comprises a nitrogen source, and the other comprises a carbon source.

(Item B12)

The method of item B11, wherein the nitrogen source is in either the first concentrated partial medium or the second concentrated partial medium at a concentration of 10 w/v % or greater.

(Item B13)

The method of item B11 or B12, wherein the carbon source is in either the first concentrated partial medium or the second concentrated partial medium at a concentration of 40 w/v % or greater.

(Item B14)

The method of any one of items B11 to B13, characterized in that a concentrated partial medium comprising the carbon source is supplied to the thermostatic vessel so that a carbon source concentration of a culture solution discharged from the thermostatic vessel is always about 0.01 w/v % or less.

(Item B15)

The method of any one of items B1 to B14, characterized in that:

1) the first concentrated partial medium, the second concentrated partial medium, and water used in the continuous manufacture are not sterilized; and
2) the first medium storage vessel, the second medium storage vessel, and the thermostatic vessel are not sterilized within 24 hours before and after the continuous manufacture of 20 hours or longer.

(Item B16)

The method of item B15, characterized in that the first medium storage vessel, the second medium storage vessel, and the thermostatic vessel are not sterilized within 72 hours before and after the continuous manufacture of 20 hours or longer.

(Item B17)

The method of any one of items B8 to B10, or items B11 to B16 that are dependent from any of items B8 to B10, characterized in that the reservoir is not sterilized within 24 hours before and after the continuous manufacture of 20 hours or longer.

(Item B18)

The method of any one of items B1 to B17, characterized in that the thermostatic vessel is operated so that a temperature of a culture solution in the thermostatic vessel would be 18 to 55° C., a dissolved oxygen concentration would be 0.1 mg/L or greater, and a pH would be 6.0 to 8.0.

(Item B19)

The method of any one of items B1 to B18, characterized in that a culture solution discharged from the thermostatic vessel comprises the microorganisms at $1\times10^9$ cells/mL or greater.

(Item B20)

The method of any one of items B1 to B19, characterized in that the microorganisms comprise at least one type selected from the group consisting of bacteria and yeasts.

(Item B21)

The method of any one of items B1 to B20, characterized in that the microorganisms comprise at least one type selected from the group consisting of gram-negative bacteria and yeasts.

(Item B22)

The method of any one of items B5 to B10, or items B11 to B21 that are dependent from any of items B5 to B10, characterized in that the spawns are prepared by removing culture supernatant from the microorganisms that have been batch-cultured, resuspending the microorganisms in a fluid free of a carbon source so that a concentration would be $1\times10^8$ to $2\times10^{10}$ cells/mL, and refrigerating the microorganisms.

(Item B23)

The method of any one of items B5 to B10, or items B11 to B21 that are dependent from any of items B5 to B10, characterized in that the spawns are prepared by diluting the microorganisms that have been batch-cultured 10-fold with a fluid free of a carbon source so that a concentration would be $1\times10^8$ to $2\times10^{10}$ cells/mL, and then refrigerating the microorganisms.

(Item B24)

The method of any one of items B5 to B10, or items B11 to B21 that are dependent from any of items B5 to B10, characterized in that the spawns are stored as dry cells of the microorganisms and suspended in a liquid so that a concentration would be $1\times10^8$ cells/mL or greater prior to being supplied to the thermostatic vessel as a spawn suspension, and a spawn suspension prepared in this manner is supplied to the thermostatic vessel.

(Item B25)

The method of any one of items B1 to B4 and B6 to B10, or items B11 to B21 that are dependent from any of items B1 to B4 and B6 to B10, characterized in that spawns of the microorganisms stored as dry cells are directly supplied to the thermostatic vessel.

(Item B26)

The method of item B24 or B25, wherein the dry cells are stored at ambient temperature.

(Item B27)

The method of any one of items B24 to B26, characterized in that the dry cells are dry cells manufactured by a step of mixing whey with the microorganisms and drying a resulting mixture under reduced pressure.

(Item B28)

A system for continuously manufacturing microorganisms, comprising:

- a thermostatic vessel;
- a blower for aerating the thermostatic vessel;
- a first medium storage vessel;
- a first pump for continuously supplying the first concentrated partial medium from the first medium storage vessel to the thermostatic vessel at constant flow rate Y1 (L/h);
- a second medium storage vessel;
- a second pump for continuously supplying the second concentrated partial medium from the second medium storage vessel to the thermostatic vessel at flow rate Q (L/h);
- a water supplying system for supplying water at constant flow rate Y2 (L/h); and
- discharging means configured to discharge a microorganism culture solution from the thermostatic vessel at constant flow rate F (L/h),
- wherein the system does not comprise a sterilization facility.

(Item B29)

The system of item B28, further comprising:

a spawn storage unit for storing a spawn suspension of the microorganisms;

a cooling system for cooling the spawn storage unit; and a third pump configured to continuously supply the spawn suspension from the spawn storage unit to the thermostatic vessel at constant flow rate X (L/h).

(Item B30)

The system of item B28, further comprising:

a spawn storage unit for storing spawns of the microorganisms as dry cells;

a spawn suspension preparation vessel comprising spawn suspension preparation vessel water supply controlling means for preparing a spawn suspension from the spawns;

dry cell supplying means configured to supply the dry cells from the spawn storage unit to the spawn suspension preparation vessel; and a fourth pump configured to continuously supply the spawn suspension from the spawn suspension preparation vessel to the thermostatic vessel at constant flow rate X (L/h).

(Item B31)

The system of item B28, characterized by further comprising:

a spawn storage unit for storing spawns of the microorganisms as dry cells; and dry cell supplying means configured to supply the dry cells from the spawn storage unit to the thermostatic vessel.

(Item B32)

The system of any one of items B29 to B31, characterized in that the spawn storage unit does not comprise a blower.

(Item B33)

The system of any one of items B28 to B32 for use in the method of any one of items B1 to B7, or items B11 to B16 and B18 to B27 that are dependent from any of items B1 to B7.

(Item B34)

A system for continuously manufacturing microorganisms, comprising:

a thermostatic vessel comprising a mechanism for detecting an amount of contents in a vessel;

a blower for aerating the thermostatic vessel;

a reservoir comprising a mechanism for detecting an amount of contents in a vessel for continuously discharging microorganisms manufactured in the thermostatic vessel while storing the microorganisms;

a first medium storage vessel;

first controlling means and a first pump for supplying a first concentrated partial medium from the first medium storage vessel to the thermostatic vessel;

a second medium storage vessel;

second controlling means and a second pump for supplying a second concentrated partial medium from the second medium storage vessel to the thermostatic vessel;

water supply controlling means that operates in conjunction with the mechanism for detecting an amount of contents in the thermostatic vessel;

first discharging means configured to continuously discharge microorganisms from the reservoir;

second discharging means configured to discharge microorganisms from the thermostatic vessel by operating in conjunction with the mechanism for detecting an amount of contents in the reservoir and to feed the microorganisms into the reservoir;

a spawn storage unit for storing a spawn suspension of the microorganisms;

a cooling system for cooling the spawn storage unit; and third controlling means and a third pump configured to supply the spawn suspension from the spawn storage unit to the thermostatic vessel;

wherein the system does not comprise a sterilization facility, characterized in that each of the first controlling means, the second controlling means, and the third controlling means operates in conjunction with the mechanism for detecting an amount of contents in the thermostatic vessel.

(Item B35)

A system for continuously manufacturing microorganisms, comprising:

a thermostatic vessel comprising a mechanism for detecting an amount of contents in a vessel;

a blower for aerating the thermostatic vessel;

a reservoir comprising a mechanism for detecting an amount of contents in a vessel for continuously discharging microorganisms manufactured in the thermostatic vessel while storing the microorganisms;

a first medium storage vessel;

first controlling means and a first pump for supplying a first concentrated partial medium from the first medium storage vessel to the thermostatic vessel;

a second medium storage vessel;

second controlling means and a second pump for supplying a second concentrated partial medium from the second medium storage vessel to the thermostatic vessel;

water supply controlling means that operates in conjunction with the mechanism for detecting an amount of contents in the thermostatic vessel;

first discharging means configured to continuously discharge microorganisms from the reservoir;

second discharging means configured to discharge microorganisms from the thermostatic vessel by operating in conjunction with the mechanism for detecting an amount of contents in the reservoir and to feed the microorganisms into the reservoir;

a spawn storage unit for storing spawns of the microorganisms as dry cells;

a spawn suspension preparation vessel comprising spawn suspension preparation vessel water supply controlling means for preparing a spawn suspension from the spawns;

dry cell supply controlling means configured to supply the dry cells from the spawn storage unit to the spawn suspension preparation vessel at a controlled timing; and fourth controlling means and a fourth pump configured to supply the spawn suspension from the spawn suspension preparation vessel to the thermostatic vessel;

wherein the system does not comprise a sterilization facility, characterized in that each of the first controlling means, the second controlling means, and the fourth controlling means operates in conjunction with the mechanism for detecting an amount of contents in the thermostatic vessel.

(Item B36)

A system for continuously manufacturing microorganisms, comprising:

a thermostatic vessel comprising a mechanism for detecting an amount of contents in a vessel;

a blower for aerating the thermostatic vessel;

a reservoir comprising a mechanism for detecting an amount of contents in a vessel for continuously discharging microorganisms manufactured in the thermostatic vessel while storing the microorganisms;

a first medium storage vessel;

first controlling means and a first pump for supplying a first concentrated partial medium from the first medium storage vessel to the thermostatic vessel;

a second medium storage vessel;

second controlling means and a second pump for supplying a second concentrated partial medium from the second medium storage vessel to the thermostatic vessel;

water supply controlling means that operates in conjunction with the mechanism for detecting an amount of contents in the thermostatic vessel;

first discharging means configured to continuously discharge microorganisms from the reservoir;

second discharging means configured to discharge microorganisms from the thermostatic vessel by operating in conjunction with the mechanism for detecting an amount of contents in the reservoir and to feed the microorganisms into the reservoir;

a spawn storage unit for storing spawns of the microorganisms as dry cells; and fifth controlling means and dry cell supplying means configured to supply the dry cells from the spawn storage unit to the thermostatic vessel;

wherein the system does not comprise a sterilization facility, characterized in that each of the first controlling means, the second controlling means, and the fifth controlling means operates in conjunction with the mechanism for detecting an amount of contents in the thermostatic vessel.

(Item B37)

The system of any one of items B34 to B36, characterized in that the spawn storage unit does not comprise a blower.

(Item B38)

The system of any one of items B34 to B37, wherein the reservoir comprises an insulating material, thermal insulation coating, and/or a heating/cooling function.

(Item B39)

The system of any one of items B34 to B38, further comprising a blower or mechanical agitation means for agitating contents of the reservoir.

(Item B40)

The system of any one of items B34 to B39 for use in the method of any one of items B8 to B10, or items B11 to B27 that are dependent from any of items B8 to B10.

Advantageous Effects of Invention

The present invention can provide a novel continuous microorganism manufacturing method and system with reduced need for sterilization to avoid germ contamination as compared to common microorganism growing methods and systems therefor.

The present invention can also provide a method for efficiently and continuously manufacturing microorganisms while economizing the amount of microorganisms used as spawns and a system therefor.

DESCRIPTION OF EMBODIMENTS

Figure 1:
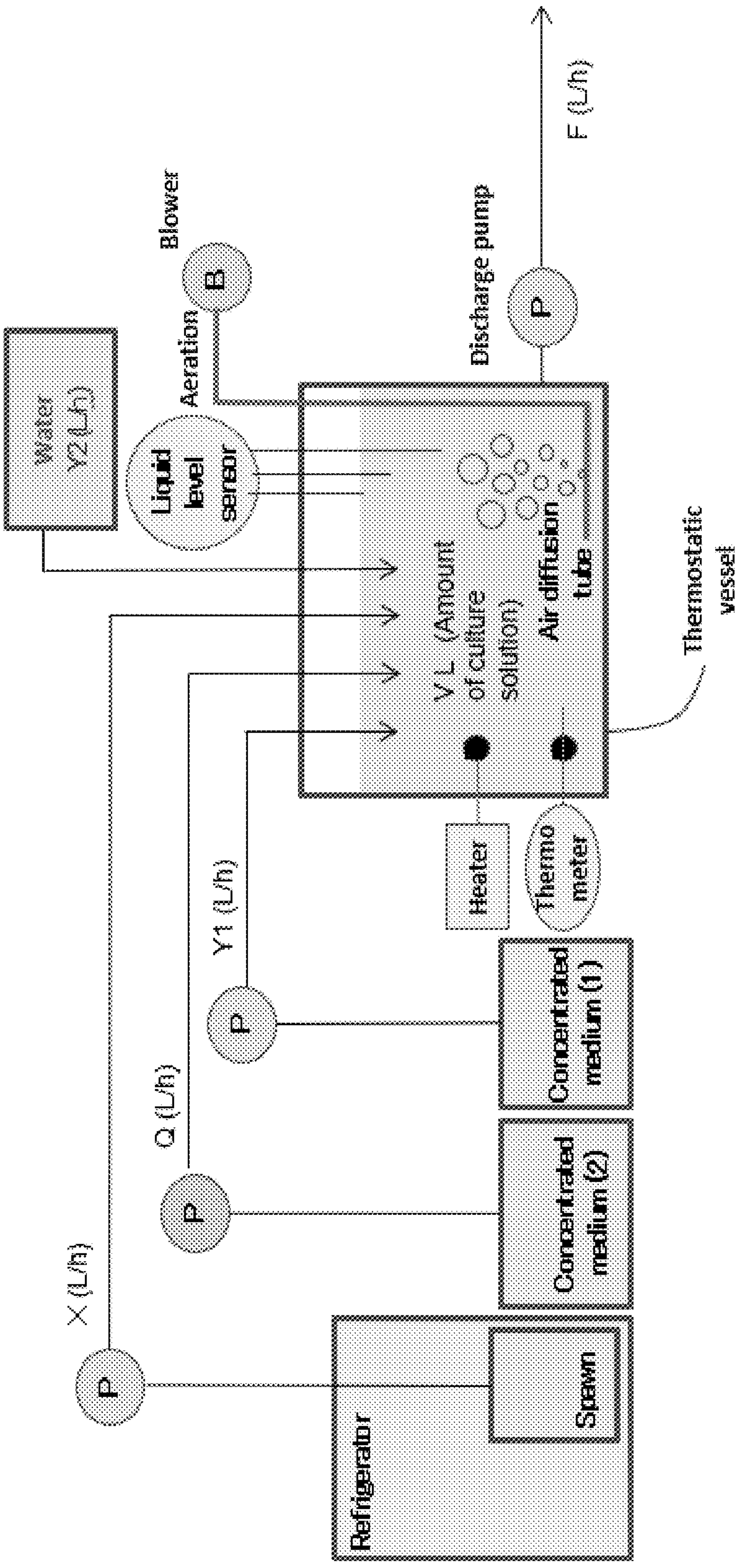
FIG. 1 is a diagram schematically showing the method and system for automatically amplifying and continuously feeding microorganisms according to embodiment 1 of the invention.

The present invention is described in detail hereinafter. Throughout the entire specification, a singular expression should be understood as encompassing the concept thereof in the plural form, unless specifically noted otherwise. Thus, singular articles (e.g., “a”, “an”, “the”, and the like in the case of English) should also be understood as encompassing the concept thereof in the plural form, unless specifically noted otherwise. Further, the terms used herein should be understood as being used in the meaning that is commonly used in the art, unless specifically noted otherwise. Therefore, unless defined otherwise, all terminologies and scientific technical terms that are used herein have the same meaning as the general understanding of those skilled in the art to which the present invention pertains. In case of a contradiction, the present specification (including the definitions) takes precedence.

1. Definitions

The definitions of the terms and/or basic technical concepts that are particularly used herein are described hereinafter.

As used herein, "comprise" encompasses the meaning of "essentially consist of)" as well as the meaning of "consist of".

As used herein, "about" refers to a numerical range of ±10% from the numerical value that is described subsequent to "about".

As used herein, flow rate, concentration, etc. that is "substantially" constant means that variation in the numerical value of the flow rate or concentration remains within the range of ±10%.

As used herein, "continuously" or "continuous" not only means that an event specified by the term takes place unceasingly, but also encompasses embodiments where the event has a period of temporary discontinuation. "Continuously" or "continuous" herein refers to a specified event taking place during a period exceeding 50% of a predetermined period (e.g., at least one hour, at least 5 hours, at least 10 hours, at least 20 hours, etc.). In a representative embodiment, "continuously" or "continuous" herein refers to a specified event taking place during a period of about 60% or more of a predetermined period (e.g., at least one hour, at least 5 hours, at least 10 hours, at least 20 hours, etc.). More typically, "continuously" or "continuous" herein refers to a specified event taking place during a period of about 70% or more of a predetermined period (e.g., at least one hour, at least 5 hours, at least 10 hours, at least 20 hours, etc.). It should be noted that "continuous" herein does not encompass an embodiment in which a specified event takes place intermittently at each given interval.

As used herein, "intermittent" refers to a specified event taking place once over a predetermined period (e.g., once every hour or more, once every 5 hours or more, once every 12 hours or more, or once every 24 hours or more). Such a predetermined period is a period of time combining a period during which a specified event takes place and a period during which the event does not take place. When "intermittent", the period during which a specified event takes place in a predetermined period is 20% or less. Typically, "intermittent" can refer to an embodiment where a period during which a specified event takes place in a predetermined period is 10% or less.

As used herein, "dry" refers to an amount of moisture excluding bound water of 5% or less, preferably 3% or less.

As used herein, "electromagnetic valve" is synonymous with "solenoid valve" and encompasses any mechanism comprising a solenoid part for converting electric energy into mechanical energy and a valve body for opening and closing a flow channel by mechanical energy converted at the solenoid part.

As used herein, "manufacture of microorganisms" does not mean that new microorganisms are created, but refers to growing certain microorganisms and newly manufacturing a large quantity of the microorganisms.

As used herein, "medium for growing microorganisms is comprised of a first medium component, a second medium component, and water" means that a medium which enables the growth of the microorganisms requires at least a first medium component and a second medium component, and the medium can additionally comprise another medium component.

As used herein, "sterilization" includes "disinfection" and refers to any treatment for killing or inactivating 99% or more, preferably 99.9% or more of the microorganisms or viruses that are contained in a medium or adhering to a manufacturing apparatus. Typically, microorganisms, etc. would not grow in a short period of time (e.g., within 24 hours, preferably 48 hours, more preferably 72 hours) after sterilization, without inoculation or new germ infiltration. Growth of microorganisms can be confirmed by using a method that is commonly practiced in the art such as visual inspection of the degree of transparency of a medium, measurement of the optical density of microorganism cells, counting colonies, or real-time PCR. The sterilization methods are typically autoclave sterilization or filter sterilization for media and carbon sources. Examples thereof for facilities such as vessels and lines include, but are not limited to, steam sterilization, dry heat sterilization, gas sterilization using ethylene oxide, formaldehyde gas, hydrogen peroxide gas, etc., sterilization through radiation or electron beam irradiation, high-pressure sterilization, etc. The methods also include methods that are described in textbooks for bioengineering, biochemical engineering, etc.

As used herein, "contamination" and "pollution" are interchangeably used, and refer to infiltration of any microorganism (yeast, bacteria, virus, etc.) other than microorganisms intended to be manufactured in the present invention.

Microorganisms manufactured by the manufacturing method of the invention can be used in the production of a useful substance, food production, and the treatment of any subject such as organic wastewater or waste. Microorganisms to be grown by the present invention are any microorganism that can assimilate a carbon source and grow. The application of microorganisms manufactured can vary in accordance with the microorganisms. When microorganisms manufactured by the present invention are used in the treatment of wastewater or waste, examples of subjects to be treated include, but are not limited to, oil and fat, mineral oil, organic chlorine compounds, hydrocarbon, aromatic compounds, organic acids, aldehydes, amines, malodorous substances, dioxin, PCB, pesticides, organic solvents, heavy metals, arsenic, etc. In one embodiment of the invention, the microorganisms of the invention can be oil and fat degrading microorganisms, and the subject of treatment can be oil and fat-containing wastewater.

2. Continuous Manufacture of Microorganisms in a Thermostatic Vessel (Embodiment 1)

The present invention is characterized by continuously supplying a first concentrated partial medium, a second concentrated partial medium, water, and optionally spawns to a thermostatic vessel, growing microorganisms in a culture solution in the thermostatic vessel at a substantially constant rate to continuously manufacture microorganisms of a desired concentration, and discharging the microorganisms comprising a substantially constant concentration of microorganisms from the thermostatic vessel at a constant flow rate to obtain microorganisms of interest. The first concentrated partial medium comprises a first medium component, the second concentrated partial medium comprises a second medium component, and a medium for growing microorganisms is comprised of the first medium component, second medium component, and water (wherein the medium can further comprise a third medium component derived from a third concentrated partial medium). In this manner, one of the features of the invention is in supplying at least two components that are essential for the growth of microorganisms individually to a thermostatic vessel in continuous manufacture of microorganisms. The method of continuously manufacturing microorganisms of the invention is continuous and is thus highly productive as compared to common manufacturing methods using batch treatment. However, conventional continuous microorganism growing methods had a high risk of contamination such as germ pollution or bacteriophage proliferation during manufacture. For this reason, facilities for continuous manufacture of microorganisms obviously require sterilization and facility therefor. Even if sterilized, it is difficult to completely prevent germ or phage pollution in the continuous manufacture of microorganisms over a long period of time (e.g., growth of residual heat resistant bacteria, unexpected infiltration of germs, etc. are possible). Thus, batch production is mainly used, while a continuous manufacturing method is applied in very few cases in actual microorganism production settings.

In this regard, it was contemplated to separate storage containers (and supply lines as needed) for a first concentrated partial medium and a second concentrated partial medium in the present invention. With such a configuration, the first concentrated partial medium does not have a second medium component required for the growth of microorganisms, and the second concentrated partial medium does not have a first medium component required for the growth of microorganisms. Thus, the growth of germs and bacteriophages in each storage container or a supply line thereof can be suppressed during continuous operation. Further, a medium that can grow microorganisms is formed by mixing a nitrogen source and a carbon source in a thermostatic vessel. Meanwhile, the growth of germs other than the microorganisms of interest can be suppressed by setting the concentration of a carbon source in the thermostatic vessel low, whereby a need for a facility and operation for sterilization can be reduced, resulting in the elimination or drastic reduction of cost associated with sterilization in a microorganism manufacturing facility and in a microorganism manufacturing method, as compared to conventional methods and facilities. This is a revolutionary advancement in the continuous manufacture of microorganisms. Simplified and compact manufacturing facilities can be achieved by reducing the need for a facility and operation for sterilization as compared to conventional art. Simplified and compact manufacturing facilities drastically reduce investment in facilities and maintenance costs in the manufacture of microorganisms, and broadly expand options for the location of installing a manufacturing facility, whereby installation in a wastewater or waste treatment plant and continuous manufacture of microorganisms on site are enabled. Of course, energy, time, and labor associated with sterilization steps are no longer required or drastically reduced, so that production cost in the manufacture of microorganisms can be markedly reduced.

The present invention does not require sterilization in this manner. Thus, in a preferred embodiment, the manufacturing method of the invention is characterized by not sterilizing a first concentrated partial medium, a second concentrated partial medium, and water supplied for diluting the concentrated partial media used in the continuous manufacture of microorganisms. In a preferred embodiment, the manufacturing method of the invention is characterized by not sterilizing a first medium storage vessel, a second medium storage vessel, and a thermostatic vessel within 24 hours, within 36 hours, within 48 hours, or within 72 hours before and after continuous manufacture of 20 hours or longer. In the manufacture of microorganisms, such facilities are generally sterilized within 24 hours of culture for the manufacture. In view of this, the lack of a need for sterilization at such a timing in the present invention is a significant advantage.

In a preferred embodiment, one of first and second medium components comprises a nitrogen source, and the other comprises a carbon source. The growth of microorganisms can be reduced significantly by storing and supplying a nitrogen source and a carbon source separately, whereby the need for sterilization is reduced. In one embodiment, a concentrated partial medium comprising a nitrogen source can comprise the nitrogen source at a concentration of about 10 w/v % or greater, about 15 w/v % or greater, preferably about 20 w/v % or greater, more preferably about 30 w/v % or greater, still preferably about 40 w/v % or greater, and still more preferably about 50 w/v %. In one embodiment, a concentrated partial medium comprising a carbon source can comprise the carbon source at a concentration of about 40 w/v % or greater, more preferably about 50 w/v % or greater, and still preferably about 60 w/v % or greater. With the presence of a high concentration of a nitrogen source and/or carbon source at a certain concentration or greater in respective concentrated media in this manner, the growth of microorganisms can be reduced due to high osmotic pressure, high salt concentration, substrate toxicity, high or low pH, etc., and contribute to reduced need for sterilization. Typically, a concentrated partial medium comprising a nitrogen source does not comprise a carbon source, and a concentrated partial medium comprising a carbon source does not comprise a nitrogen source.

In a preferred embodiment, embodiment 1 is characterized by growing microorganisms at a substantially constant rate in a thermostatic vessel and is characterized in that the microorganism concentration of a culture solution discharged from a thermostatic vessel is constant during continuous production. This generally requires that the flow rate of a fluid supplied to a thermostatic vessel is equal to the flow rate of a fluid discharged from the thermostatic vessel. However, the inventor discovered that this can be achieved by setting the concentration of one of at least two concentrated partial media very high (50 w/v % or greater, preferably 60 w/v % or greater, more preferably 70 w/v % or greater, still preferably 80 w/v % or greater, still more preferably 90 w/v % or greater, and most preferably 100%) and suitably adjusting the supply flow rate (typically, the medium volume (Q) of second concentrated partial medium supplied every hour) so that discharge flow rate F of a culture solution from a thermostatic vessel is nearly equal to the sum (Y) of medium volume Y1 of a first concentrated partial medium supplied every hour and volume Y2 of water supplied every hour. For example, batch culture such as that in Patent Literature 1 does not achieve growth of a substantially constant rate or discharge of a culture solution comprising a substantially constant concentration of microorganisms.

In a preferred embodiment, embodiment 1 is characterized in that discharge flow rate F is set to $\frac{1}{30}$ to $\frac{1}{2}$, more preferably $\frac{1}{12}$ to $\frac{1}{2}$ of thermostatic vessel volume V, whereby the residence time can be appropriately set, and the possibility of growth of germs can be reduced. Specifically, if the residence time is set to be the same as the time of continuous manufacture, a culture solution in a thermostatic vessel is replaced with a fresh culture solution at a timing matching the continuous manufacture time. If the residence time is set to be half of the time of the continuous manufacture, a culture solution in a thermostatic vessel would be replaced twice with a fresh culture solution during the continuous manufacture. Replacement of a culture solution promotes infiltrated germs to be discharged from a thermostatic vessel instead of growing in the thermostatic vessel. Meanwhile, the residence time of microorganisms in a thermostatic vessel can be a time that can maintain a substantially constant concentration without reducing the concentration of the microorganisms of interest in a culture solution discharged from the thermostatic vessel. For culture in a continuous system, microorganisms grown during the residence time are always present in a thermostatic vessel. Thus, the residence time can be shortened as compared to batch culture, which must wait until fed microorganisms grow to a certain level. Shortening the residence time can maintain the microorganisms of interest that are always present in the thermostatic vessel at a constant concentration while eliminating newly infiltrated germs from the thermostatic vessel before the infiltrated germs grow.

The present invention can also reduce the volume of a thermostatic vessel for growing microorganisms in accordance with the residence time of microorganisms as compared to, for example, conventional microorganism manufacturing methods for growing microorganisms by batch culture every 24 hours, etc. If the residence time of microorganisms is 12 hours, the volume of a thermostatic vessel can be ½ as compared to, for example, a method of growing microorganisms by batch culture every 24 hours, etc. While a residence time of 12 hours is difficult in some cases in a system for growing microorganisms in a thermostatic vessel by batch culture, this is possible in a continuous system such as the present invention.

Installation conditions of a thermostatic vessel can be considered more flexibly by reducing the volume of the thermostatic vessel in this manner. This allows installation even in a small factory lot. The entire system for treatment can be configured to be compact by disposing a thermostatic vessel near the location where the manufactured microorganisms are used (e.g., a vessel for treating wastewater or waste, which is the subject of treatment).

(Spawns)

In this embodiment, a suspension of spawns of microorganisms of a predetermined concentration (e.g., $1\times10^6$ to $1\times10^{12}$ cells/mL, preferably $1\times10^8$ to $2\times10^{10}$ cells/mL) may be added at constant flow rate X (L/h) to a thermostatic vessel. A preferred embodiment in such a case is characterized in that the sum of constant flow rate X and medium flow rate Y is configured to be equal to constant flow rate F discharged from a thermostatic vessel.

In this embodiment, spawns may be stored in a form of a suspension in a spawn storage unit, or stored in a spawn storage unit as dry cells. A manufacturing method for dry cells is described in detail below. In one embodiment, spawns are stored as dry cells of microorganisms, and prepared as a spawn suspension prior to being supplied to the thermostatic vessel. The spawn suspension is suspended in a liquid so that the concentration thereof would be a predetermined concentration (e.g., $1\times10^8$ to $2\times10^{10}$ cells/mL) and continuously supplied to the thermostatic vessel for 20 hours or longer at constant flow rate X (L/h) as described above, or prepared to have a concentration of $k\times2\times10^{10}$ cells/mL or greater ($k\geq1$) and the spawn suspension is continuously supplied to the thermostatic vessel for 20 hours or longer at constant flow rate Z (L/h), wherein the relationship between constant flow rates X and Z is $Z=X/k$. In such a case, a preferred embodiment is characterized in that (Z+Y) is equal to constant flow rate F discharged from a thermostatic vessel. In another embodiment of the invention, dry cells are directly supplied to the thermostatic vessel so that the microorganism concentration would be $1\times10^8$ cells/mL or less. After reaching the intended concentration, microorganisms may be supplied to a thermostatic vessel continuously or intermittently.

In one embodiment, the spawns of the invention can be prepared by removing culture supernatant from cultured (typically, batch-cultured) microorganisms, resuspending the resulting microorganisms in any fluid free of a carbon source such as an inorganic salt medium, buffer, or water so that the concentration would be a predetermined concentration (e.g., $1\times10^6$ to $1\times10^{12}$ cells/mL, preferably $1\times10^8$ to $2\times10^{10}$ cells/mL), and refrigerating the microorganisms. The spawns of the invention can be resuspended so that the concentration would be preferably $1\times10^8$ to $9\times10^9$ cells/mL, more preferably $1\times10^8$ to $2\times10^9$ cells/mL. Preferably, a fresh inorganic salt medium free of a carbon source is used as the fluid. In another embodiment of the invention, the spawns of the invention can be prepared by diluting the cultured microorganisms 10-fold with any fluid free of a carbon source such as an inorganic salt medium, buffer, or water, and refrigerating the microorganisms. A fluid used for dilution can preferably be an inorganic salt medium free of a carbon source.

Spawns are commonly stored directly in a culture solution in the art. Aeration can be necessary to maintain the viability rate in this state. However, the inventor discovered that the viability rate of spawns can be maintained without aeration with a blower for spawns prepared by removing culture supernatant from batch-cultured microorganisms, resuspending the resulting microorganisms in a fluid (e.g., fresh medium) free of a carbon source, and refrigerating the microorganisms. In a preferred embodiment, a medium for growing microorganisms can comprise a carbon source, nitrogen, phosphorous, potassium, etc., and the fluid for resuspension after growth can be an inorganic salt medium free of a carbon source. Alternatively, the effect of culture supernatant can be reduced by diluting a culture solution 10-fold with a fluid free of a carbon source (e.g., inorganic salt medium or water free of a carbon source). Even if there is a residual carbon source, the concentration thereof can be sufficiently reduced. Thus, the inventor discovered that the viability rate of spawns can be maintained without aeration in the same manner as those prepared by removing culture supernatant and resuspending microorganisms in a fresh medium free of a carbon source.

(Thermostatic Vessel)

The thermostatic vessel of the invention preferably comprises a thermoregulator and a thermometer, and can control the temperature during microorganism culture (amplification). The temperature is typically controlled to 18 to 55° C., preferably 25 to 42° C., and more preferably 28 to 37° C. When the temperature is outside of such a temperature range, the temperature can be appropriately adjusted by heating or cooling. A water level gauge or a liquid level sensor may be installed in a thermostatic vessel to enable sensing and controlling at least the lower limit and upper limit, and in some cases, the middle level of the liquid surface. The liquid level sensor may also serve the role of a foam sensor, or a system for sensing foaming through another principle may be installed. The thermostatic vessel can comprise a system for automatically supplying a defoamer by operating in conjunction with such a system for sensing foaming.

The present invention may perform aeration and agitation to supply air, which is required for the growth of microorganisms, in a thermostatic vessel. Agitation is performed by mixing a culture solution to contact microorganisms to be grown with a medium and carbon source to promote growth of the microorganisms. The specific means for aeration or agitation is not limited. In a preferred embodiment, the thermostatic vessel of the invention comprises a blower. A blower can introduce air as well as agitate and mix a culture. Alternatively, air introducing means (e.g., air pump) for mechanical aeration and agitation may be used concomitantly with agitation means (e.g., agitation mixer with an agitation blade).

Since the oxygen dissolution efficiency is higher at a deeper air diffusing location for aeration in a thermostatic vessel due to water pressure from the water depth, an air diffusion tube of a blower is preferably provided at a lower portion of the thermostatic vessel to supply air from the lower portion of the thermostatic vessel.

It is desirable to maintain the dissolved oxygen concentration (DO) in a thermostatic vessel generally at 0.05 mg/L or higher, preferably 0.1 mg/L or higher, through aeration and agitation means such as a blower.

The pH of a culture solution in a thermostatic vessel is generally within the range of 4.5 to 9.0, preferably 5.5 to 8.5, and more preferably 6.0 to 8.0. When the pH is outside of these ranges, the pH can be appropriately adjusted by adding an acid or alkali.

Microorganisms in a thermostatic vessel can be grown so that a continuously discharged microorganism-containing culture solution comprises microorganisms at a predetermined concentration (e.g., $1\times10^9$ cells/mL) or greater.

In a preferred embodiment, two thermostatic vessels described above may be provided, and each thermostatic vessel may be operated for each predetermined condition. In this regard, a culture solution in one of the two thermostatic vessels can be completely discharged from the thermostatic vessel in accordance with a predetermined condition at a predetermined timing (e.g., every 1 day to 1 month, 1 day to 30 days, 1 day to 15 days, 1 day to 10 days, 1 to 7 days, etc.). This period is not considered as a continuously operating period. Y=F described below does not hold during this period. A medium of a predetermined volume (e.g., 90 to 100%, 95 to 100%, 95 to 99%, etc. of the volume) of a discharged culture solution may then be resupplied to the thermostatic vessel, and a spawn suspension of microorganisms of a predetermined concentration (e.g., $1\times10^8$ to $1\times10^{10}$ cells/mL) may be supplied to the thermostatic vessel so that the volume would be a predetermined volume (e.g., 10 to 0.1%, 5 to 0.1%, 10 to 1%, 5 to 1%, etc. of the volume) of a discharged culture solution, and the thermostatic vessel may be aerated for a predetermined period of time (e.g., 12 to 24 hours, 18 to 24 hours, etc.) to grow the microorganisms in the thermostatic vessel for a moment. Alternatively, the entire culture solution in one of the two thermostatic vessels may be discharged at a predetermined timing (e.g., every 1 day to 1 month, 1 day to 30 days, 1 day to 15 days, 1 day to 10 days, 1 to 7 days, etc.) in accordance with a predetermined condition, then a medium of the same volume as the discharged culture solution may be resupplied to the thermostatic vessel, and dry cells of spawns of the microorganisms may be supplied so that a microorganism concentration in the thermostatic vessel would be a predetermined concentration (e.g., $1\times10^6$ to $1\times10^8$ cells/mL), and the microorganisms may be aerated for a predetermined period of time (e.g., 12 to 24 hours, 18 to 24 hours, etc.) to grow the microorganisms in the thermostatic vessel for a moment. These can be considered maintenance work for the thermostatic vessel. As described above, the present invention can shorten the residence time, so that the volume of a thermostatic vessel can be reduced. Thus, a plurality of thermostatic vessels with a low volume can be provided, which enables separation of a continuously producing thermostatic vessel from a thermostatic vessel under maintenance. For example, washing, water-pouring, dechlorination by aeration, feeding of a concentrated medium, and inoculation of spawns can be performed for each complete culture solution discharging operation of each thermostatic vessel at a timing in accordance with a predetermined condition. The continuous supply of spawns is generally stopped during maintenance. An embodiment with two thermostatic vessels was described above as an example, but an embodiment of providing three or four thermostatic vessels in parallel and switching thermostatic vessels being used at a timing in accordance with a predetermined condition is also within the scope of the present invention. After discharging a culture solution, one or both of the following steps can be performed before supplying spawns of microorganisms: (1) an operation to supply and drain water one or more times before supplying a concentrated partial medium to wash a thermostatic vessel; and (2) an operation to aerate for a while after supplying water to eliminate chlorine in water.

Examples of predetermined conditions for switching thermostatic vessels used when a plurality of thermostatic vessels are provided include, but are not limited to, passage of a certain period of time, change in pH, change in DO, foaming, change in lipase activity, change in substrate concentration, amount of acid or alkali added exceeding a specified value, total amount of medium (including concentrated medium) supplied exceeding a specified value, etc. The time until the occurrence of a change in pH, change in DO, foaming, change in lipase activity, change in substrate concentration, etc. may be measured, and the passage of time may be used as the predetermined condition. Alternatively, the predetermined condition can be about 400 t minutes (t is the time (minutes) required for cell division of microorganisms under culture conditions in a thermostatic vessel).

(Flow Rate)

FIG. 1 schematically shows the method and system for continuously manufacturing microorganisms of the invention.

As shown in FIG. 1, a first concentrated partial medium (e.g., nitrogen source), a second concentrated partial medium (e.g., carbon source such as oil and fat, alcohol, or lactic acid), and water are continuously fed to a thermostatic vessel. Such continuous feeding and continuous discharge of a culture solution from the thermostatic vessel can typically be performed for 20 hours or longer. In one embodiment, such continuous feeding and discharge can be performed for about 20 hours, followed by washing, re-feeding of a medium, and aeration for dechlorination, and continuous feeding and discharge can be performed again for about 20 hours. Spawns may be additionally fed to the thermostatic vessel.

FIG. 1 shows an embodiment of storing spawns in a refrigerator as a suspension. It is apparent from the descriptions elsewhere that the present invention is not necessarily limited to a form of storing spawns as a suspension. For the spawns in FIG. 1, a suspension of microorganisms at a predetermined concentration (e.g., $1\times10^8$ to $2\times10^{10}$ cells/mL) is stored in a refrigerator and is added to the thermostatic vessel at a flow rate of X (L/h). Microorganisms stored as dry cells can also be directly supplied to the thermostatic vessel. In such a case, the dry cells can be supplied so that the microorganism concentration would be, for example, a predetermined concentration (e.g., $1\times10^8$ cells/mL) or less in the thermostatic vessel. Microorganisms may be supplied to the thermostatic vessel continuously or intermittently.

The first concentrated partial medium (e.g., nitrogen source, etc.) is added at Y1 (L/h), the second concentrated partial medium (e.g., carbon source such as oil and fat, alcohol, or lactic acid) is added at Q (L/h), and water is added at Y2 (L/h) to a thermostatic vessel.

For example in FIG. 1, the first concentrated partial medium is configured to be free of a carbon source, so that the first concentrated partial medium does not have a carbon source required for the growth of microorganisms, and the second concentrated partial medium contains a carbon source, but lacks a medium component such as a nitrogen source required for growth. Thus, growth of germs and bacteriophages in each storage container and supply line thereof can be suppressed during continuous operation.

Flow rate X of a supply of a spawn suspension is 1/500 to 1/50, and can typically be 1/100 or less of medium flow rate Y. Spawns are diluted to 1/500 to 1/50 upon addition to a thermostatic vessel. By culturing the diluted spawns, a microorganism culture solution comprising microorganisms with a concentration that is 1 to 10-fold of the spawn solution can be ultimately manufactured. The concentration of microorganisms in a culture solution can be $1\times10^9$ cells/mL or greater.

In a preferred embodiment, flow rate X of feeding a spawn suspension is typically greater than 0, but can be an amount that can be ignored relative to flow rate Y (Y1+Y2). Thus, F=Y can be true. Alternatively, spawns are not fed during continuous operation of 20 hours or longer, i.e., X can be 0. In such a case, of course F=Y holds true.

A microorganism-containing culture solution with a constant microorganism concentration is discharged at constant flow rate F (L/h) from a thermostatic vessel. A culture solution discharged from a thermostatic vessel can comprise microorganisms at $1\times10^9$ cells/mL. In a preferred embodiment, flow rate F is equal to Y when a spawn suspension is not supplied, and is equal to X+Y when a spawn suspension is supplied at flow rate X. When a spawn suspension is supplied, the spawn suspension (X)+second concentrated partial medium (e.g., carbon source) Q+medium (Y=Y1+Y2) are fed to the thermostatic vessel at a constant flow rate, while flow rate F corresponding to X+Y is discharged at a constant flow rate. As described above, X can be Y/100 or less. Thus, X can be an amount that can be ignored relative to Y. In such a case, Y would be equal to F. It should be noted that flow rate (Q) of a second concentrated partial medium (e.g., carbon source) is not considered with regard to discharge flow rate F in the present invention. Even for continuous operation, microorganisms in a thermostatic vessel are living organisms, so it is challenging to maintain the activity constant for a long period of time. Since activity has a range of variability, consumption of a carbon source, etc. also has a range of variability. For this reason, the amount of culture solution and medium concentration in a thermostatic vessel cannot be readily maintained at a constant value in conventional continuous operation that adjusts the total amount flowing into the thermostatic vessel to be the same as the total amount flowing out from the thermostatic vessel. Thus, a large number of microorganism concentration sensors, carbon source concentration sensors, etc. must be used. Meanwhile, the present invention determines the amount of discharge while ignoring the amount of addition of a carbon source by adjusting the total amount flowing into the thermostatic vessel other than the carbon source to be the same as the total amount flowing out from the thermostatic vessel while ignoring the flow volume of the carbon source, so that the present invention is less susceptible to the variability in consumption of a carbon source during continuous operation. Thus, the operation of a microorganism manufacturing facility is readily stabilized. In another embodiment, the invention is operated by including a nitrogen source in a second concentrated partial medium and including a carbon source in a first concentrated partial medium to achieve X+Y=F as described above. In such a case, Y would be the flow rate of supply of a medium comprising a carbon source. In this manner, the operator can appropriately determine which concentrated partial medium comprises either a carbon source or a nitrogen source.

A carbon source can be supplied to a thermostatic vessel as a second concentrated partial medium such that the carbon source concentration of a culture solution in the thermostatic vessel is always at a predetermined concentration (e.g., about 0.01 w/v %) or less. Thus, a carbon source in a microorganism-containing culture solution discharged from a thermostatic vessel can have a concentration of about 0.01 w/v % or less. The carbon source concentration of a culture solution in a thermostatic vessel exceeding a predetermined concentration (e.g., about 0.01 w/v %) and/or the carbon source concentration in a culture solution discharged from a thermostatic vessel exceeding a predetermined concentration (e.g., about 0.01 w/v %) can be addressed by reducing flow rate Q of a carbon source being supplied, extending the residence time in the thermostatic vessel, or both. The carbon source concentration in a thermostatic vessel can be controlled to a predetermined concentration or less to reduce the possibility of unintended contamination by microorganisms in the thermostatic vessel. A carbon source concentration of a culture solution in a thermostatic vessel refers to the weight of a carbon source relative to the volume of the entire culture solution. Obviously, it can be understood that the carbon source concentration can locally exceed the predetermined concentration in some parts supplied with a carbon source in a culture solution, but the carbon source concentration in the culture solution can still be at or below the predetermined concentration. “Always” described above means “always” during continuous supply of medium, carbon source, and optionally spawns to a thermostatic vessel, continuous manufacture of microorganisms in the thermostatic vessel, and continuous discharge of a microorganism-containing culture solution from the thermostatic vessel.

In another preferred embodiment, a nitrogen source is supplied to a thermostatic vessel as a second concentrated partial medium so that the nitrogen source concentration of a culture solution in the thermostatic vessel is always at a predetermined concentration (e.g., about 0.01 w/v %) or less. For this reason, a nitrogen source in a microorganism-containing culture solution discharged from a thermostatic vessel can be at a concentration of about 0.01 w/v % or less. In another embodiment, a nitrogen source is included in a second concentrated medium as ammonium, and the nitrogen source can be supplied only by the amount needed as a continuous pH-stat operated in conjunction with pH control of a culture solution. In such a case, it is preferable to include a carbon source in a first concentrated medium. Such an embodiment can also be within the scope of the instant patent.

In a particularly preferred embodiment, the present invention can supply a nitrogen source and a carbon source to a thermostatic vessel through separate storage containers and supply lines to suppress growth of germs and bacteriophages in each storage container or supply line thereof during continuous operation, but the growth of germs and bacteriophages in the entire manufacturing apparatus can be suppressed by suppressing the carbon source concentration (or nitrogen source concentration) of a culture solution in the thermostatic vessel to a predetermined concentration or less. Controlling the carbon source concentration in a culture solution in a thermostatic vessel can be readily achieved by adjusting the total amount flowing into the thermostatic vessel other than the carbon source to be equal to the total amount flowing out from the thermostatic vessel while ignoring the flow volume of the carbon source. For the materialization thereof, it is important to supply the carbon source as a high concentration of a concentrated partial medium and control the carbon source concentration in a thermostatic vessel to a predetermined concentration or lower.

(Apparatus and System)

The present invention can also provide an apparatus or system for use in the method of continuously manufacturing microorganisms according to embodiment 1 of the invention. The apparatus or system of the invention typically comprises a spawn storage unit (e.g., about 15 to 500 L), a first medium (e.g., 300× concentrated medium) storage vessel (e.g., about 5 to 50 L), a second medium storage vessel (can have a smaller volume than the first medium storage vessel, such as about 4 to 40 L), and a thermostatic vessel for culturing and growing spawns to manufacture microorganisms (e.g., about 4 to 500 L), and the apparatus or system is for the continuous manufacture of a substantially constant concentration of microorganisms for 20 hours or longer (FIG. 1).

The thermostatic vessel for amplifying spawn microorganisms of the invention can be a metal, plastic, or glass vessel with a cylindrical or rectangular tube shape. Preferably, a thermostatic vessel comprises a thermoregulator and a thermometer and can control the temperature during microorganism culture (amplification). The temperature is typically controlled to 18 to 55° C., preferably 25 to 42° C., and more preferably 28 to 37° C. A water level gauge or a liquid level sensor may be installed within a thermostatic vessel to enable sensing and controlling at least the lower limit and upper limit, and in some cases the middle level of the liquid surface. The liquid level sensor may also serve the role of a foam sensor, or a system for sensing foaming through another principle may be installed. The thermostatic vessel can comprise a system for automatically supplying a defoamer that operates in conjunction with such a system for sensing foaming. In a typical embodiment, a thermostatic vessel can comprise a blower. An air diffusion tube or air diffusion ball, or a microbubble/nanobubble generator may be installed in a thermostatic vessel.

A medium is stored in a medium storage vessel and supplied to a thermostatic vessel at a constant flow rate. A medium storage vessel is typically made of metal, plastic, or glass, preferably plastic or metal. A medium storage vessel may be stored in a refrigerator. In a preferred embodiment, a medium storage vessel is a tank for storing a concentrated medium, i.e., a medium storage vessel, and water can be supplied from another line (FIG. 1).

A carbon source is stored in a medium storage vessel, which is typically made of metal, plastic, or glass, preferably plastic or metal.

The spawn storage unit in the apparatus or system of the invention is a portion for storing microorganisms that are the source of an inoculated species prior to being cultured in a thermostatic vessel (storage vault or storage vessel). The spawn storage unit of the invention is typically made of metal, plastic, or glass, but the material is not limited thereto. In a representative embodiment, the spawn storage unit of the invention does not comprise a blower for aeration. In FIG. 1, the spawn storage unit is stored in a refrigerator, but the configuration is not necessarily limited thereto. Especially when spawns are stored as dry cells, cooling during storage is not required, and spawns can be stored at ambient temperature.

The method of the present invention can use a plurality of types of microorganisms as spawns. The plurality of types of microorganisms may be stored in a plurality of storage tanks by each type. Preferably, a plurality of types of microorganisms may be stored in one storage tank or in a number of storage tanks that is less than the number of types of microorganisms. Storage of a plurality of types of microorganisms in a low number (preferably one) of storage tanks makes the preparation of the system and spawns simple and efficient.

Although not illustrated, the system of the invention may further comprise another tank or apparatus. For example, the system may comprise tanks for storing each of an organic matter other than a carbon source of microorganisms or a solution thereof, defoaming agent, pH adjusting agent, etc.

The system of the invention can comprise: a first pump configured to continuously supply a first concentrated partial medium from a first medium storage vessel to a thermostatic vessel at constant flow rate Y1 (L/h); a second pump configured to continuously supply a second concentrated partial medium (e.g., carbon source) from a second medium storage vessel to the thermostatic vessel at flow rate Q (L/h); a water supplying system for supplying water at constant flow rate Y2 (L/h); and discharging means configured to discharge a microorganism-containing culture solution from the thermostatic vessel at constant flow rate F (L/h) (Y1+Y2=Y). The discharging means can be any means for automatically draining a culture solution in a thermostatic vessel so that the amount of the culture solution in the thermostatic vessel would be substantially constant. For example, the means may be a pump configured to discharge a microorganism-containing culture solution from a thermostatic vessel at constant flow rate F (L/h), or a discharge tube installed at an intended height of a thermostatic vessel.

In an embodiment of storing a spawn suspension in a spawn storage unit, the system of the invention can further comprise a third pump configured to continuously supply the spawn suspension from the spawn storage unit to the thermostatic vessel at constant flow rate X (L/h).

In an embodiment of storing spawns in a spawn storage unit as dry cells, the dry cells may be supplied to a spawn suspension preparation vessel to form a spawn suspension before addition to a thermostatic vessel, or may be directly added to the thermostatic vessel. Dry cells can be added to a spawn suspension preparation vessel or thermostatic vessel by dry cell supplying means, and any powder feeder known in the art can be used as the dry cell supplying means. In order to add a predetermined concentration of dry cells to a spawn suspension preparation vessel or thermostatic vessel, the added weight and/or time of addition can be controlled for the addition of the dry cells from a feeder to each vessel.

In an embodiment comprising a spawn suspension preparation vessel, the system of the invention can further comprise a fourth pump configured to continuously supply a spawn suspension to the thermostatic vessel at constant flow rate X (L/h).

The continuous microorganism manufacturing apparatus and system of the invention do not comprise a facility for sterilization. Sterilization in this regard is sterilization through steam sterilization, gas sterilization using ethylene oxide, etc., or radiation or electron beam irradiation.

3. Combination of Batch Style Thermostatic Vessel and Reservoir (Embodiment 2)

Figure 7:
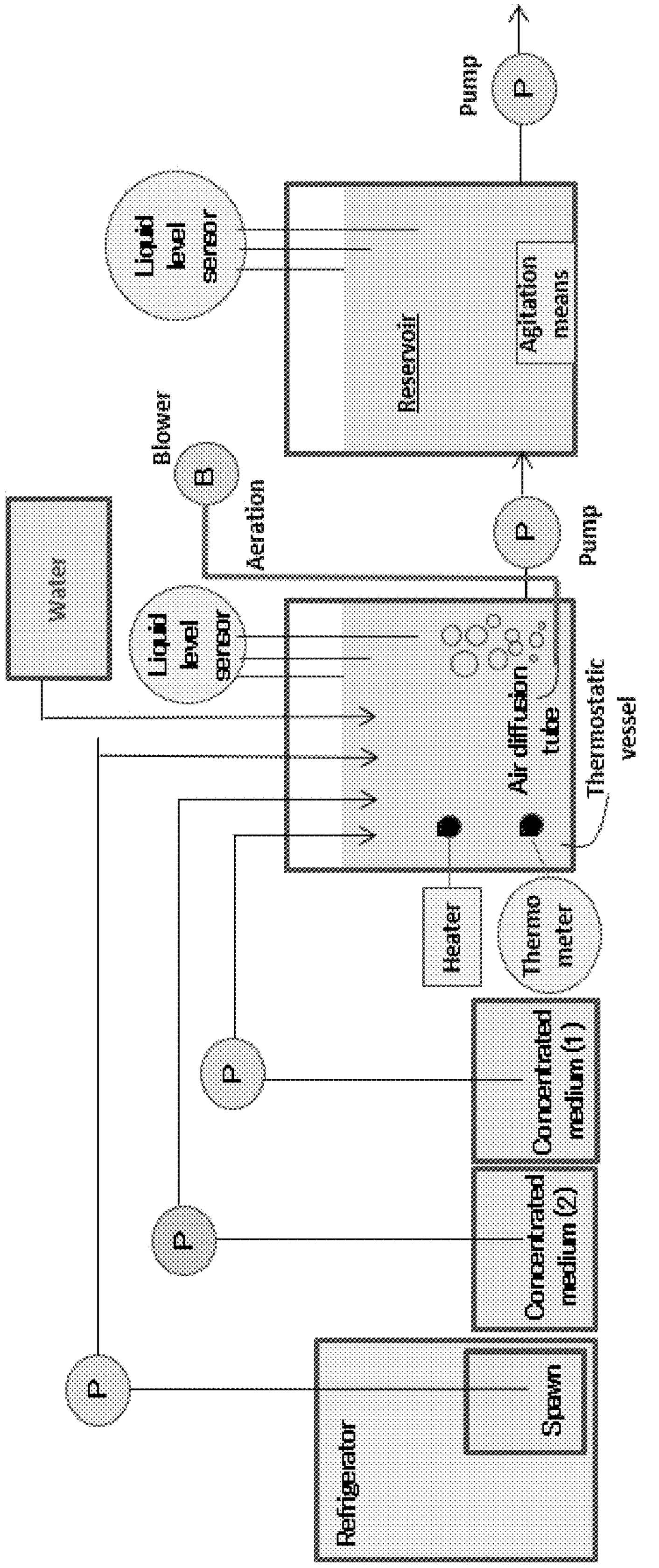
FIG. 7 is a diagram schematically showing the method and system for automatically amplifying and continuously feeding microorganisms according to embodiment 2 of the invention.

The present invention also provides a method and system for culturing spawn microorganisms in a batch style thermostatic vessel, transferring the microorganisms to a reservoir associated therewith, and continuously discharging a culture solution from the reservoir, in addition to embodiment 1 described above for continuously culturing spawn microorganisms in the thermostatic vessel (see FIG. 7). While the methods of automatically amplifying microorganisms differ between embodiment 1 and embodiment 2, the embodiments are the same in terms of continuously manufacturing a constant concentration of microorganisms at a constant flow rate.

(Reservoir)

The method of this embodiment stores a microorganism-containing culture solution from growing spawns in a reservoir and continuously discharges a culture solution comprising a substantially constant concentration of microorganisms to manufacture microorganisms. A reservoir comprises any means for identifying the amount of culture solution in the reservoir. Means for identifying the contents of culture solution in a reservoir may be, but are not limited to, a water level gauge, a liquid level sensor, etc. for identifying the position of the liquid surface of the culture solution, or a weight scale, etc. for identifying the weight of the culture solution in the reservoir. In a preferred embodiment, the present invention can install a water level gauge or a liquid level sensor in a reservoir to identify that the amount of culture solution in the reservoir has decreased beyond a threshold value from the liquid surface. When the decrease of culture solution in the reservoir has reached the threshold value in such a case, the culture solution containing microorganisms grown in the thermostatic vessel is transferred to the reservoir.

Means for identifying the amount of contents in a reservoir (e.g., a water level gauge or a liquid level sensor) can detect at least the lower limit (microorganism-containing culture solution has run out or at a level close to running out) and preferably can also detect the upper limit (e.g., full or at a level close to full).

The reservoir of the invention can comprise a system for sensing foaming (e.g., foam sensor). The liquid level sensor described above may also serve the role of a foam sensor. In a preferred embodiment, the reservoir can also comprise a system for automatically supplying a defoaming agent by operating in conjunction with a system for sensing foaming.

The reservoir of the invention is preferably constructed to have a configuration for retaining heat. Specifically, heat is retained by an insulating material or insulation coating. Insulation material or insulation coating may be directly applied to a reservoir, or a reservoir may be installed in a box configured for retaining heat in such a manner. Alternatively, a reservoir may be able to control the temperature of a microorganism-containing culture solution in a reservoir by comprising a thermoregulator and thermometer. However, such a configuration is costly, so a thermoregulator is not essential. The temperature in a reservoir is typically 0 to 42° C., preferably 4 to 40° C. When outside of these temperature ranges, the temperature can be appropriately adjusted by heating or cooling.

A reservoir may be agitated so that microorganisms would not sink to the bottom. The specific means for agitation are not limited. In a preferred embodiment, the reservoir of the invention comprises a blower for agitation and mixing. Alternatively, the reservoir may comprise a mechanical agitation means (e.g., an agitation mixer with an agitation blade or oscillating agitator). A blower in a reservoir does not need to move an amount of air to the extent in microorganism culture in a thermostatic vessel described below, etc. The amount can be 80% or less, 70% or less, 60% or less, 50% or less, etc., such as 40 to 80%, 40 to 70%, or 40 to 60%, of the amount of air used in aeration of a thermostatic vessel.

Since the purpose of a blower in a reservoir is to prevent precipitation of microorganisms, it is preferable that an air diffusion tube of the blower is provided at a lower portion of the reservoir, and air is supplied from the lower portion of the reservoir.

A microorganism-containing culture solution replenishing a reservoir from a thermostatic vessel can comprise, for example, microorganisms at $1\times10^9$ cells/mL or greater. A user can appropriately adjust the amount of discharge of microorganisms manufactured in this embodiment in accordance with the usage of the microorganisms.

(Thermostatic Vessel)

The thermostatic vessel of the invention comprises a thermoregulator and a thermometer and can control the temperature during microorganism culture (amplification). The temperature is typically controlled to 18 to 55° C., preferably 25 to 42° C., and more preferably 28 to 37° C. When the temperature is outside of such temperature ranges, the temperature can be appropriately adjusted by heating or cooling. Any means (e.g., water level gauge or a liquid level sensor) for identifying the amount of contents (amount of culture solution or water) in a thermostatic vessel is installed in the vessel to enable sensing and controlling at least the lower limit and upper limit, and in some cases the middle level of the liquid surface. The liquid level sensor may also serve the role of a foam sensor, or a system for sensing foaming through another principle may be installed. The thermostatic vessel can comprise a system for automatically supplying a defoamer by operating in conjunction with such a system for sensing foaming.

The contents that decreases by transferring a microorganism-containing culture solution to a reservoir can be identified to be decreased beyond a threshold value by means for identifying the amount of contents in a thermostatic vessel (e.g., water level gauge or a liquid level sensor). When the decrease in the amount of microorganism-containing culture solution in a thermostatic vessel reaches a threshold value, spawns, first concentrated partial medium (e.g., medium containing a nitrogen source but is free of a carbon source), second concentrated partial medium (e.g., carbon source free of a nitrogen source), water, etc. are supplied to the thermostatic vessel and batch-cultured to newly manufacture microorganisms. When the amount of microorganism-containing culture solution in the thermostatic vessel decreases again beyond the threshold value, the solution can be transferred to the reservoir. The first concentrated partial medium comprises a first medium component, and the second concentrated partial medium comprises a second medium component. A medium for growing microorganisms is comprised of the first medium component, second medium component, and water (wherein the medium can further comprise a third medium component derived from a third concentrated partial medium). In this embodiment, the first concentrated partial medium and the second concentrated partial medium are individually stored and supplied in the same manner as embodiment 1 described above. Thus, an effect of reduced need for sterilization can be achieved. It should be noted that batch-culturing is performed to newly manufacture a microorganism-containing culture solution in a thermostatic vessel at a timing when the amount of a microorganism-containing culture solution in the reservoir has decreased to a threshold value, so that batch-culture in the thermostatic vessel is not periodically performed in this embodiment.

The thermostatic vessel of the invention further comprises various controlling means for automatically starting to supply water and each of first concentrated partial medium/second concentrated partial medium/spawns in response to the water level detected by means for identifying the amount of contents in the vessel (e.g., a water level gauge or a liquid level sensor) and various supplying means (e.g., pump) controlled thereby in accordance with the water level. The controlling means can be any means for opening and closing a flow channel in response to the water level, but can typically be a valve, especially an electromagnetic valve.

A thermostatic vessel can be designed so that aeration and growing of new microorganisms can be performed after supplying water and first concentrated partial medium/second concentrated partial medium/spawns. The thermostatic vessel can also be designed to dechlorinate by supplying spawns after aerating for about several minutes to one hour before supplying the spawns. Furthermore, a thermostatic vessel may be controlled with a program for, after supplying water and before supplying first concentrated partial medium/second concentrated partial medium/spawns, detecting the water level and repeating draining and resupplying water for washing. A thermostatic vessel can be washed by, after supplying water, draining water in response to the water level detected by a water level gauge or a liquid level sensor of the thermostatic vessel exceeding the upper threshold value, resupplying water in response to the water level detected in the thermostatic vessel exceeding the lower threshold value, and repeating the draining and resupplying any number of times (e.g., 1 to 10 times). A drainage channel may be provided to the thermostatic vessel, separately from a line for transferring a culture solution to a reservoir, for draining in the washing step. Each of the steps such as "amplification (production) of microorganisms", "dechlorination", and "washing" are programmed, and a user can make an appropriate selection to perform the selected step.

The present invention may perform aeration and agitation for supplying air, which is required for the growth of microorganisms, in a thermostatic vessel. Agitation is performed by mixing a culture solution to contact microorganisms to be grown with a medium and carbon source to promote the growth of the microorganisms. The specific means for aeration or agitation is not limited. In a preferred embodiment, the thermostatic vessel of the invention comprises a blower. A blower can introduce air as well as agitate and mix a culture. Alternatively, air introducing means (e.g., air pump) for mechanical aeration and agitation may be used concomitantly with mechanical agitation means (e.g., agitation mixer with an agitation blade or oscillating agitator).

Since the oxygen dissolution efficiency is higher at a deeper air diffusing location for aeration in a thermostatic vessel due to water pressure from the water depth, an air diffusion tube of a blower is preferably provided at a lower portion of the thermostatic vessel to supply air from the lower portion of the thermostatic vessel.

It is desirable to maintain the dissolved oxygen concentration (DO) in a thermostatic vessel generally at 0.05 mg/L or higher, preferably 0.1 mg/L or higher through aeration and agitation means such as a blower.

The pH of a culture solution in a thermostatic vessel is generally within the range of 4.5 to 9.0, preferably 5.5 to 8.5, and more preferably 6.0 to 8.0. When the pH is outside of these ranges, the pH can be appropriately adjusted by adding an acid or alkali.

Microorganisms in a thermostatic vessel can be grown until the concentration is $1\times10^9$ cells/mL or greater.

The thermostatic vessel of the invention can comprise a function for transferring a culture solution from the thermostatic vessel to a reservoir at a timing of detecting that the amount of a microorganism-containing culture solution has reached a threshold value (e.g., the liquid surface of the culture solution has decreased to the threshold value) in the reservoir described above. For example, a pump, a liquid transporting tube, etc. can serve the function for transferring a culture solution from a thermostatic vessel to a reservoir.

One embodiment of embodiment 2 can also comprise a step of washing a reservoir by repeating sending water used in washing a thermostatic vessel to the reservoir and draining water accumulated in the reservoir from the reservoir one to several times. To rapidly transfer washing water from a thermostatic vessel to a reservoir and drain washing water from the reservoir, a high-speed liquid transferring/draining means may be provided, in addition to a discharging system used in draining of culture solution, in the thermostatic vessel and reservoir.

The amount and/or residence time of a carbon source supplied as a second concentrated partial medium can be set so that the carbon source concentration in a microorganism-containing culture solution discharged from a thermostatic vessel would be a predetermined concentration (e.g., about 0.05 w/v % or less, about 0.01% w/v or less, or about 0.001 w/v % or less), preferably 0. The carbon source concentration may be measured in a culture solution discharged from a thermostatic vessel to change the amount of supply and/or residence time of a carbon source in accordance with the results of measurement. For example, when the carbon source concentration of a culture solution discharged from a thermostatic vessel is set to about 0.01 w/v % or less, the amount of carbon source supplied may be reduced, the residence time may be extended, or both if the carbon source concentration of a culture solution discharged from the thermostatic vessel exceeds about 0.01 w/v %. The carbon source concentration of a culture solution discharged from the thermostatic vessel can be controlled to a predetermined concentration or less to reduce the possibility of unintended contamination by microorganisms in the reservoir after transferring the culture solution.

Embodiment 2 can similarly benefit from the advantage of embodiment 1, i.e., sterilization would no longer be needed by separating a first concentrated partial medium from a second concentrated partial medium (e.g., separate a carbon source from other medium components). The need for sterilization of a reservoir can be further reduced by controlling the carbon source concentration of a culture solution discharged from a thermostatic vessel to a predetermined concentration or lower.

In another preferred embodiment, the nitrogen source concentration in a microorganism-containing culture solution discharged from a thermostatic vessel and transferred to a reservoir can be set to a predetermined concentration (e.g., about 0.05 w/v % or less, about 0.01% w/v or less, or about 0.001 w/v % or less), preferably 0. In still another embodiment, a nitrogen source is included in a second concentrated medium as ammonium, and the nitrogen source can be supplied only by the amount needed as a continuous pH-stat operated in conjunction with pH control of a culture solution, whereby the nitrogen source concentration in the microorganism-containing culture solution discharged from the thermostatic vessel and transferred to the reservoir is suppressed to a predetermined concentration or less. In such a case, it is preferable to include a carbon source in a first concentrated medium. Such an embodiment can also be within the scope of the instant patent.

In a preferred embodiment, a first medium component comprises a nitrogen source and a second medium component comprises a carbon source. The growth of bacteria or microorganisms can be reduced significantly by storing and supplying a nitrogen source and a carbon source separately, whereby the need for sterilization is reduced. In one embodiment, a first concentrated partial medium can comprise a nitrogen source at a concentration of about 10 w/v % or greater, about 15 w/v % or greater, preferably about 20 w/v % or greater, more preferably about 30 w/v % or greater, still preferably about 40 w/v % or greater, and still more preferably about 50 w/v % or greater. In one embodiment, a concentrated partial medium comprising a carbon source can comprise the carbon source at a concentration of about 40 w/v % or greater, more preferably about 50 w/v % or greater, and still preferably about 60 w/v % or greater. With the presence of a high concentration of a nitrogen source and/or carbon source at a certain concentration or greater in respective concentrated media in this manner, the growth of microorganisms can be reduced due to high osmotic pressure, high salt concentration, substrate toxicity, high or low pH, etc., to contribute to reduced need for sterilization. Typically, a concentrated partial medium comprising a nitrogen source does not comprise a carbon source, and a concentrated partial medium comprising a carbon source does not comprise a nitrogen source.

The present invention does not require sterilization in this manner. Thus, in a preferred embodiment, the manufacturing method of the invention is characterized by not sterilizing a first concentrated partial medium or a second concentrated partial medium used in the manufacture of microorganisms. In a preferred embodiment, the manufacturing method of the invention is characterized by not sterilizing a first medium storage vessel, a second medium storage vessel, a thermostatic vessel, or a reservoir within 24 hours, within 36 hours, within 48 hours, or within 72 hours before and after continuous manufacture of 20 hours or longer. In the manufacture of microorganisms, such facilities are generally sterilized within 24 hours of culture for the manufacture. In view of this, the lack of a need for sterilization at such a timing in the present invention is a significant advantage.

(Spawns)

In this embodiment, a spawn suspension of microorganisms with a concentration of $1\times10^{6}$ to $1\times10^{12}$ cells/mL, preferably $1\times10^{8}$ to $2\times10^{10}$ cells/mL may be added to a culture solution with a volume of about 50 to 500-fold in a thermostatic vessel.

Spawns may be stored in a form of a suspension in a spawn storage unit, or stored in a spawn storage unit as dry cells. A manufacturing method for dry cells is described in detail below. In one embodiment of the invention, spawns are stored as dry cells of microorganisms, and prepared as a spawn suspension prior to being supplied to the thermostatic vessel. The spawn suspension may be suspended in a liquid so that the concentration thereof would be $1\times10^{8}$ to $2\times10^{10}$ cells/mL and added to the thermostatic vessel as described above, or prepared to have a concentration of $k\times2\times10^{10}$ cells/mL or greater ($k\geq1$) and the spawn suspension may be supplied to the thermostatic vessel (wherein the spawn suspension is added to a culture solution with a volume of about 50 k to 500 k-fold). In another embodiment of the invention, dry cells are directly supplied to the thermostatic vessel so that the microorganism concentration would be $1\times10^{8}$ cells/mL or less.

In one embodiment, the spawns of the invention can be prepared by removing culture supernatant from microorganisms that have been cultured (typically, batch-cultured), resuspending the resulting microorganisms in any fluid free of a carbon source such as an inorganic salt medium, buffer, or water so that a concentration would be $1\times10^{6}$ to $1\times10^{12}$ cells/mL, preferably $1\times10^{8}$ to $2\times10^{10}$ cells/mL, and refrigerating the microorganisms. The spawns of the invention can be resuspended so that the concentration would be preferably $1\times10^{8}$ to $9\times10^{9}$ cells/mL, more preferably $1\times10^{8}$ to $2\times10^{9}$ cells/mL. Preferably, a fresh inorganic salt medium free of a carbon source is used as the fluid. In another embodiment of the invention, the spawns of the invention can be prepared by diluting the cultured microorganisms 10-fold with any fluid free of a carbon source such as an inorganic salt medium, buffer, or water, and refrigerating the microorganisms. A fluid used for dilution can preferably be an inorganic salt medium free of a carbon source.

Spawns are commonly stored directly in a culture solution in the art. Aeration can be necessary to maintain the viability rate in this state. However, the inventor discovered that the viability rate of spawns can be maintained without aeration with a blower for spawns prepared by removing culture supernatant from batch-cultured microorganisms, resuspending the resulting microorganisms in a fluid (e.g., fresh medium) free of a carbon source, and refrigerating the microorganisms. In a preferred embodiment, a medium for growing microorganisms can comprise a carbon source, nitrogen, phosphorous, potassium, etc., and the fluid for resuspension after growth can be an inorganic salt medium free of a carbon source. Alternatively, the effect of culture supernatant can be reduced by diluting a culture solution 10-fold with a fluid free of a carbon source (e.g., inorganic salt medium or water free of a carbon source). Even if there is residual carbon source, the concentration thereof can be sufficiently reduced. Thus, the inventor discovered that the viability rate of spawns can be maintained without aeration in the same manner as those prepared by removing culture supernatant and resuspending in a fresh medium free of a carbon source.

(Operation Cycle)

The method and system according to embodiment 2 can be operated in the following cycle.

1. Set the Amount of Discharge with a Discharge Amount Controller

The amount of discharge from a reservoir is set in accordance with the production schedule for a product (microorganism suspension).

2. Discharge

A microorganism culture solution is stably obtained as a product by operating a discharge pump to achieve the set discharge amount, and continuously discharging a culture solution comprising microorganisms with a constant concentration from a reservoir at a constant flow rate.

3. Detect a State of Low Water Level of a Microorganism-Containing Culture Solution in a Reservoir A water level gauge detects that the culture solution level has decreased due to step 2, and the level has reached or exceeded a threshold value.

4. Transfer of a Culture Solution from the Thermostatic Vessel

The entire amount of culture solution in the thermostatic vessel is transferred to the reservoir in response to the detection in step 3.

5. Regrowing Microorganisms 5-1. The process returns to step 2 and the microorganism-containing culture solution is discharged from the reservoir, and 5-2. Water is supplied to the thermostatic vessel, and heating, aeration, and feeding of spawns/first concentrated partial medium/second concentrated partial medium are performed therein to batch culture microorganisms. The specific operation flow can be the following.

5-2-1. The water level in the thermostatic vessel decreased by the step of transferring a culture solution from the thermostatic vessel to the reservoir in step 4 is detected by a water level gauge or a liquid level sensor. If the culture solution level has reached or exceeded the threshold value, the controlling means of a water supply port is opened to start supplying water.

5-2-2. Once the water level has been elevated by supplying water and reaches the threshold value, the controlling means of the water supply port is closed to stop supplying water, and the controlling means of supply ports for first concentrated partial medium/second concentrated partial medium/spawns are opened to supply a certain amount of each of first concentrated partial medium, second concentrated partial medium, and spawns to the thermostatic vessel.

5-2-3. Aeration is started, and microorganisms are cultured and amplified for a certain period of time to manufacture a microorganism-containing culture solution.

While the cycle of steps 2 to 5 described above is repeated, the culture solution manufactured in step 5-2 (5-2-3) would be the culture solution in the thermostatic vessel in step 4.

The cycle may further comprise the following steps between steps 5-2-1 and 5-2-2 described above.

A. The thermostatic vessel is drained again after detecting that water has been supplied to the thermostatic vessel up to a predetermined amount (e.g., thermostatic vessel is full, etc.), and water is resupplied by detecting that the water level has decreased to a threshold value, and the draining and supplying water are repeated any number of times thereafter to wash the inside of the thermostatic vessel.

B. After supplying water, aeration is performed for a certain period of time for dechlorination.

A and B may be performed each time step 5-2 described above is performed, A and B may be set to be performed after step 5-2 has been performed any number of times, or a user may be able to operate the invention to perform A and B at any timing. After step 5-2 described above is performed, A may be performed but not B, or B may be performed but not A. This can be appropriately set by the user in accordance with the circumstance.

Washing water generated in step A described above may be discharged from a drainage port provided separately on the thermostatic vessel, or may be transferred to the reservoir and then discharged from the reservoir by a culture solution discharge pump of the reservoir or through a drainage port provided separately. The reservoir can be washed subsequent to the thermostatic vessel by the latter method.

(Apparatus and System)

The present invention can also provide an apparatus or system for use in the method of continuously manufacturing microorganisms according to embodiment 2 of the invention. The apparatus or system of the invention typically comprises a spawn storage unit (e.g., about 15 to 500 L), a first medium storage vessel (e.g., about 5 to 50 L), a second medium storage vessel (can have a smaller volume than the first medium storage vessel, such as about 4 to 40 L), a thermostatic vessel for culturing and growing spawns to grow microorganisms (e.g., about 100 to 500 L), and a reservoir for storing a microorganism-containing culture solution (i.e., about 100 to 500 L), and the apparatus or system is for continuously (e.g., continuously for 24 hours or longer) discharging a microorganism-containing culture solution with a substantially constant concentration from the reservoir (FIG. 7).

The thermostatic vessel and reservoir can be a metal, plastic, or glass vessel with a cylindrical or rectangular tube shape. The thermostatic vessel has discharging means for discharging a microorganism-containing culture solution to the reservoir, and the reservoir has discharging means for discharging a stored microorganism-containing culture solution. The thermostatic vessel and reservoir can further have discharging means for rapidly discharging washing water, etc. in addition to the discharging means for a culture solution.

A thermostatic vessel comprises a thermoregulator and a thermometer and can control the temperature during microorganism culture (amplification). The temperature is typically controlled to 18 to 55° C., preferably 25 to 42° C., and more preferably 28 to 37° C. A thermostatic vessel comprises any means (e.g., a water level gauge or a liquid level sensor) for identifying the amount of contents in the vessel (amount of culture solution or water).

The thermostatic vessel of the invention also comprises the following means, which operate in response to (operating in conjunction with) the water level detected by means for identifying the amount of contents in the vessel (e.g., a water level gauge or a liquid level sensor):

first medium controlling means and a pump for automatically supplying a first concentrated partial medium from a first medium storage vessel to a thermostatic vessel;

second medium controlling means and a pump for automatically supplying a second concentrated partial medium from a second medium storage vessel to a thermostatic vessel;

spawn controlling means and spawn pump/feeder configured to supply spawns to the thermostatic vessel; and water supply controlling means.

It is preferable that each of the first medium controlling means, second medium controlling means, and spawn controlling means is automatically operated in conjunction with a mechanism for detecting the amount of contents in the thermostatic vessel. In this regard, "operate in conjunction with a mechanism for detecting the amount of contents in the thermostatic vessel" includes directly operating in conjunction in response to a signal for the amount of water detected by the mechanism for detecting the amount of contents in the thermostatic vessel, as well as indirectly operating in conjunction with the mechanism for detecting the amount of contents in the thermostatic vessel via another valve or pump in response to a behavior of another valve or pump operating in conjunction with a signal for water level detected by the mechanism for detecting the amount of contents in the thermostatic vessel. For example, when a signal indicating that the water level in a thermostatic vessel has met a certain threshold value or condition is emitted by a mechanism for detecting the amount of contents in the thermostatic vessel, the first medium controlling means opens a flow channel by operating in conjunction therewith to supply a first concentrated partial medium into the thermostatic vessel by a culture pump. In such a case, the first medium controlling means "directly" operates in conjunction with the mechanism for detecting the amount of contents in the thermostatic vessel. Second medium controlling means and spawn controlling means can be set to detect the operation of the first medium controlling means or medium pump and operate in conjunction therewith. In such a case, the second medium controlling means and spawn controlling means "indirectly" operate in conjunction with the mechanism for detecting the amount of contents in the thermostatic vessel. Each of the first medium controlling means, second medium controlling means, and spawn controlling means may directly operate in conjunction with the mechanism for detecting the amount of contents in the thermostatic vessel, or one of the first medium controlling means, second medium controlling means, and spawn controlling means may directly operate in conjunction with the mechanism for detecting the amount of contents in the thermostatic vessel, and the other two may indirectly operate in conjunction with the mechanism for detecting the amount of contents in the thermostatic vessel, or two of the first medium controlling means, second medium controlling means, and spawn controlling means may directly operate in conjunction with the mechanism for detecting the amount of contents in the thermostatic vessel and the other one may indirectly operate in conjunction with the mechanism for detecting the amount of contents in the thermostatic vessel.

The aforementioned spawn controlling means and spawn pump and/or spawn feeder are:

(i) controlling means and a pump for supplying a spawn suspension from a spawn storage unit to a thermostatic vessel when the spawn suspension is stored in the spawn storage unit, (ii) spawn suspension preparation vessel water supply controlling means for controlling water supply to a spawn suspension preparation vessel, dry cell supply controlling means for supplying dry cells from a spawn storage unit to the spawn suspension preparation vessel, and controlling means and a pump for supplying a spawn suspension from the spawn suspension preparation vessel to a thermostatic vessel when dry cells are stored in the spawn storage unit and the dry cells are prepared into a spawn suspension in the spawn suspension preparation vessel, and the spawn suspension is supplied to the thermostatic vessel, or (iii) controlling means and a spawn feeder for supplying dry cells from a spawn storage unit to a thermostatic vessel when the dry cells are stored in the spawn storage unit and the dry cells are supplied to the thermostatic vessel.

In case of (ii) (i.e., when dry cells are stored in a spawn storage unit and the dry cells are prepared into a spawn suspension in the spawn suspension preparation vessel, and the spawn suspension is supplied to the thermostatic vessel), supply of water or supply of dry cell spawns to the spawn suspension preparation vessel and supply of a spawn suspension to the thermostatic vessel can be controlled operably in conjunction with the amount of contents in a spawn preparation vessel and the status of control in the thermostatic vessel (draining, water supply, supply of medium, etc.), respectively.

A thermostatic vessel also comprises discharging means for discharging a culture solution from the thermostatic vessel in response to (operating in conjunction with) detecting that the amount of culture solution in a reservoir has reached the lower limit by a water level gauge or a liquid level sensor.

In a preferred embodiment, each of water supply controlling means, first medium controlling means, second medium controlling means, and spawn controlling means can directly operate in conjunction with the water level in a thermostatic vessel, or the water supply controlling means can directly operate in conjunction with the water level in a thermostatic vessel, and the first medium controlling means, second medium controlling means, and spawn controlling means can operate in conjunction with the water supply controlling means to indirectly operate in conjunction with the water level in the thermostatic vessel.

Water supply controlling means may open in conjunction with the level of culture solution in a thermostatic vessel decreasing beyond a threshold value, and automatically close after sensing an elevation in the water level in the thermostatic vessel or after supplying a certain amount of water.

In a preferred embodiment of the invention, controlling means can be an electromagnetic valve.

A reservoir comprises any means (e.g., a water level gauge or a liquid level sensor) for identifying the amount of contents in the vessel (amount of culture solution or water).

Various controlling means, pumps, and/or discharging means operating in conjunction with the water level in the thermostatic vessel or reservoir can be controlled with a micro-controller, etc. integrated with a program or the like specifying the amount of manufacture, number of washing, etc.

A reservoir is preferably constructed to have a configuration for retaining heat. Specifically, heat is retained by an insulating material or insulation coating. Insulation material or insulation coating may be directly applied to a reservoir, or a reservoir may be installed in a box configured for retaining heat in such a manner. Alternatively, a reservoir may be able to control the temperature of a culture solution in a reservoir by comprising a thermoregulator and thermometer, but this is not essential.

A reservoir may comprise a blower or a mechanical agitation means (e.g., an agitation mixer with an agitation blade or oscillating agitator) for agitation and mixing to prevent precipitation of microorganisms.

A first concentrated partial medium is stored in a first medium storage vessel and is automatically supplied to a thermostatic vessel by an operation in conjunction with the water level in the thermostatic vessel. A first medium storage vessel is typically made of metal, plastic, or glass, preferably plastic or metal. A first medium storage vessel may be stored in a refrigerator.

A second concentrated partial medium is stored in a second medium storage vessel and is automatically supplied to a thermostatic vessel by an operation in conjunction with the water level in the thermostatic vessel. A second medium storage vessel is typically made of metal, plastic, or glass, preferably plastic or metal. A second medium storage vessel may be stored in a refrigerator.

The spawn storage unit in the apparatus or system of the invention is a portion for storing microorganisms that are the source of an inoculated species prior to being cultured in a thermostatic vessel (storage vault or storage vessel). A spawn storage unit has means for automatically supplying spawns to a thermostatic vessel or a spawn suspension preparation vessel by operating in conjunction with the water level in a thermostatic vessel. The spawn storage unit of the invention is typically made of metal, plastic, or glass, but the material is not limited thereto. In a representative embodiment, the spawn storage unit of the invention does not comprise a blower for aeration. In FIG. 7, the spawn storage unit is stored in a refrigerator, but the configuration is not necessarily limited thereto. Especially when spawns are stored as dry cells, cooling during storage is not required, and they can be stored at ambient temperature.

In the method of the invention, a plurality of types of microorganisms can be used as spawns. The plurality of types of microorganisms may be stored in a plurality of storage tanks by each type. Preferably, a plurality of types of microorganisms may be stored in one storage unit or in a number of storage units that is less than the number of types of the microorganisms. Storage of a plurality of types of microorganisms in a low number (preferably one) of storage units makes the preparation of a system and spawns simple and efficient.

Although not illustrated, the system of the invention may further comprise another tank or apparatus. For example, the system may comprise tanks for storing each of an organic matter other than a carbon source of microorganisms or a solution thereof, defoaming agent, pH adjusting, etc.

The continuous microorganism manufacturing apparatus and system of the invention do not comprise a facility for sterilization. Sterilization in this regard is sterilization through steam sterilization, gas sterilization using ethylene oxide, etc., or radiation or electron beam irradiation.

4. Carbon Source

Carbon sources that can be used in the present invention are described hereinafter. Carbon sources described hereinafter are applicable to both embodiments 1 and 2 described above.

A carbon source used in the present invention can be any carbon source that microorganisms can consume and grow. Microorganisms grow by consuming a carbon source and converting the amount of consumption multiplied by cell yield into cell components. In general, growth of microorganisms is difficult under the presence of a high concentration of any compound that can be a carbon source. It is understood that this is due to osmotic pressure, substrate toxicity, etc. With compounds having higher substrate toxicity, growth of microorganisms becomes more difficult even at a lower concentration, and with compounds having lower substrate toxicity, microorganisms can grow unless the concentration is increased higher. Thus, for any carbon source, the need for sterilization can be reduced by storing the carbon source at a high concentration to the extent that growth of microorganisms is difficult. In a preferred embodiment, a carbon source is stored in a second medium storage vessel as a second concentrated partial medium. A carbon source with high substrate toxicity or recalcitrance can reduce the need for sterilization even without a high concentration. Thus, in a preferred embodiment, a carbon source with a high substrate toxicity is used. However, in another preferred embodiment, even carbon sources which have low substrate toxicity and are readily degraded can be used by creating a state in which growth of microorganisms is difficult through storage at a high concentration. A carbon source is stored in a state in which growth of microorganisms is difficult in the present invention. Since it can be challenging to clearly determine a threshold value or extent of properties of a compound such as substrate toxicity or recalcitrance with respect to microorganisms targeted for manufacture, whether growth of microorganisms is difficult may be determined appropriately through an experiment, etc. A state in which growth of microorganisms is difficult can be determined by inoculating, for example, *E. coli, Bacillus subtilis*, baker's yeast, etc. at, for example, $1\times10^6$ to $1\times10^8$ cells/mL, and observing that microorganisms left standing for 24 hours at 25 to 37° C. do not grow 10-fold or more, etc. Examples of carbon sources with high substrate toxicity include alcohols (e.g., ethanol, methanol, isopropanol, and butanol), organic solvents (e.g., toluene, ethyl acetate, dimethyl ether, diethyl ether, and alkane), chlorine compounds (e.g., chloroform, trichloroethylene, and trichloroacetic acid), etc. Examples of recalcitrant carbon sources include oil and fat, mineral oil, dioxane, polycyclic aromatic compounds, etc.

The carbon source of the invention may use one or a plurality of carbon sources as needed. Organic waste, waste oil, or waste comprising oil discharged from a food factory, restaurant industry, etc. may also be used. The carbon source of the invention is typically a liquid, but may be provided in a form of powder. A carbon source, when in a form of powder, can be added to a thermostatic vessel, supply line, mixing vessel, etc. through a supply system such as a powder feeder from a medium storage vessel.

In a preferred embodiment of either embodiment 1 or 2 described above, a carbon source and a partial medium comprising a nitrogen source are stored separately and supplied to a thermostatic vessel separately from respective supply lines, and the carbon source, nitrogen source, and other medium components are mixed in the thermostatic vessel. This is because one of a carbon source and a nitrogen source required for the growth of microorganisms would be lacking in a storage vessel with such a configuration, so that germ pollution can be avoided. However, the present invention is not limited thereto. A second concentrated partial medium comprising either a nitrogen source or a carbon source and a first concentrated partial medium comprising a carbon source or a nitrogen source, which is not contained in the second concentrated partial medium, may be mixed in a mixing vessel or supply line prior to being supplied to a thermostatic vessel, or a concentrated partial medium comprising a carbon source and a nitrogen source may be stored in a second storage vessel and supplied to a thermostatic vessel through a supply line, and mixed with a medium comprising other components required for growth in the thermostatic vessel.

The present invention does not require sterilization of a carbon source or nitrogen source, a storage vessel thereof, or a supply line thereof. In other words, the carbon source or nitrogen source of the invention may be appropriately selected by those skilled in the art from the viewpoint of the lack of a need to sterilize a storage vessel.

5. First Concentrated Partial Medium

A first concentrated partial medium that can be used in the present invention is described hereinafter. In a preferred embodiment, a first concentrated partial medium is free of a carbon source and constitutes a medium for growing microorganisms in combination with a carbon source (and other additional components as needed). The first concentrated partial medium typically comprises at least a nitrogen source. In another embodiment, a first concentrated partial medium is free of a nitrogen source and constitutes a medium for growing microorganisms in combination with a nitrogen source (and other additional components as needed). the first concentrated partial medium typically comprises at least a carbon source. The media described below can be applied to both embodiments 1 and 2 described above.

In a preferred embodiment, a first concentrated partial medium can be prepared by concentrating a medium that is commonly used in microorganism culture and preferably can comprise phosphorous, potassium, etc. Such a medium that is supplemented with a nitrogen source or carbon source and concentrated can be a first concentrated partial medium. A medium comprising a nitrogen source may be an inorganic salt medium. An example of the composition of an inorganic salt medium can be 3.5 g/L of $Na_2HPO_4$, 2.0 g/L of $KH_2PO_4$, 4 g/L of $(NH_4)_2SO_4$, 0.34 g/L of $MgCl_2 \cdot 6H_2O$, 2.8 mg/L of $FeSO_4 \cdot 7H_2O$, 2.4 mg/L of $MnSO_4 \cdot 5H_2O$, 2.4 mg/L of $CoCl_2 \cdot 6H_2O$, 1.7 mg/L of $CaCl_2 \cdot 2H_2O$, 0.2 mg/L of $CuCl_2 \cdot 2H_2O$, 0.3 mg/L of $ZnSO_4 \cdot 7H_2O$, and 0.25 mg/L of $NaMoO_4$. Since the medium in such a case is free of a carbon source, the medium does not necessarily need to be refrigerated. The nitrogen source in the medium of such a case is ammonium sulfate $(NH_4)_2SO_4$.

In the present invention, a first concentrated partial medium and water may be each directly added to a thermostatic vessel to generate a medium with a concentration of interest in the thermostatic vessel, or may be mixed in a mixing vessel or supply line prior to being added to a thermostatic vessel to produce a medium with a concentration of interest and then added to the thermostatic vessel.

A first concentrated partial medium can have a concentration of about 10-fold or greater, about 50-fold or greater, about 100-fold or greater, about 200-fold or greater, and preferably about 250-fold or greater of medium components with a concentration of interest in a thermostatic vessel.

6. Nitrogen Source

In a preferred embodiment, a nitrogen source that can be contained in either a first concentrated partial medium or second concentrated partial medium is an inorganic salt such as ammonium sulfate, other ammonium salt, nitrate, or nitrite. Amino acids, etc. can also be a nitrogen source, but they can also be a carbon source, so amino acids, etc. are not suitable for storing a nitrogen source and a carbon source separately. While urea is an organic compound comprising carbon, urea is utilized in microorganisms by first decomposing the urea into ammonium and carbon dioxide by hydrolysis. Thus, urea can generally be a nitrogen source, but not a carbon source. This is because heterotrophic microorganisms utilizing organic matter as a carbon source cannot immobilize carbon dioxide. Accordingly, urea can be considered as a nitrogen source, which cannot be a carbon source. In another preferred embodiment, a nitrogen source that can be contained in either a first concentrated partial medium or a second concentrated partial medium is urea.

In another preferred embodiment, a first concentrated partial medium comprises a carbon source, and a second concentrated partial medium comprises a nitrogen source. In such a case, the same compound described above can be used as a nitrogen source, but urea or ammonium is particularly preferable. Ammonium water can also be supplied as a pH-stat for the culture solution in a thermostatic vessel. For example, 15% ammonium water is strongly alkaline with a pH of about 11, under which normal microorganisms cannot grow. Thus, 15% ammonium water is suitable as a second concentrated partial medium comprising a nitrogen source.

7. Microorganisms (Properties of Microorganisms)

The microorganisms targeted for continuous manufacture in the present invention can be any microorganism that are heterotrophic microorganisms which can assimilate a carbon source used and grow. The specific type of microorganisms can be appropriately selected by those skilled in the art in accordance with the objective. Examples thereof include oil and fat degrading bacteria, mineral oil degrading bacteria, organic solvent assimilating bacteria, alcohol assimilating bacteria, organic contaminant assimilating bacteria, *E. coli, Bacillus subtilis*, budding yeasts, fission yeast, lactic acid bacteria, polysaccharide degrading bacteria, etc. Such microorganisms may be a wild-type strain, genetically recombinant strain, or mutant strain. Taxonomically, microorganisms can be eubacteria, gram-negative bacteria, gram-positive bacteria, *Actinomyces*, yeasts, mold (filamentous bacteria), archaea, etc.

Microorganisms used in embodiment 1 and embodiment 2 described above are not particularly different. One type alone or two or more types of microorganisms can be mixed and used as the microorganisms manufactured in the invention. When two or more types are mixed and used, it is desirable to combine and use symbiotic microorganisms.

An example of oil and fat degrading microorganisms include microorganisms with an ability to degrade 80% or more of oil and fat and fatty acid in a hydrolysis product corresponding to n-Hex value=10000 mg/L within 72 hours, preferably 48 hours, more preferably 36 hours, and still more preferably 24 hours under the conditions of 22 to 35° C., pH=5.5 to 8.5, DO≥0.1 mg/L, and batch culture.

Spawns of microorganisms can be manufactured through culturing by a known method.

(Spawn Suspension)

In a preferred embodiment, the spawn suspension of the invention can be obtained, for example, through the following steps. The volumes can be adjusted in accordance with the circumstances.

1. Culturing step: Microorganisms are cultured in an inorganic salt medium (e.g., 10 L) supplemented with a carbon source by batch culture until reaching $1\times10^8$ to $2\times10^{10}$ cells/mL. For example, the composition described above can be used as the composition of the inorganic salt medium.
2. Harvesting step: The culture solution obtained in the culturing step described above is, for example, centrifuged (e.g., under conditions of 2000×g, 15 min, and 25° C.), and pellet-like wet cell clumps are retrieved.
3. Resuspension step: The harvested wet cell clumps are resuspended in a medium (e.g., 100 L of inorganic salt medium which is not supplemented with a carbon source) to prepare a spawn suspension.
4. Storing step: Optionally, the suspension is placed in a storage container (e.g., 200 L), and a lid is placed thereon to shield light for incubating and storing the suspension at 4° C. Aeration with a blower is not required for storing the spawn suspension of the invention obtained in this manner. This is an advantageous feature of the invention. Aeration with a blower at a constant interval was required for storing a spawn suspension of microorganisms in conventional art, but a blower for aerating a spawn suspension is not required in the system of the invention, so that cost can be reduced.

The wet cell clumps described above can be obtained by roughly separating a culture solution into cell clumps and culture supernatant and removing the culture supernatant by any means that is known in the art, such as centrifugation, or filtration, coagulation and settling, or compactive dewatering.

Microorganisms may be grown in the culturing step described above by continuous culture or fed-batch culture.

Figure 2:
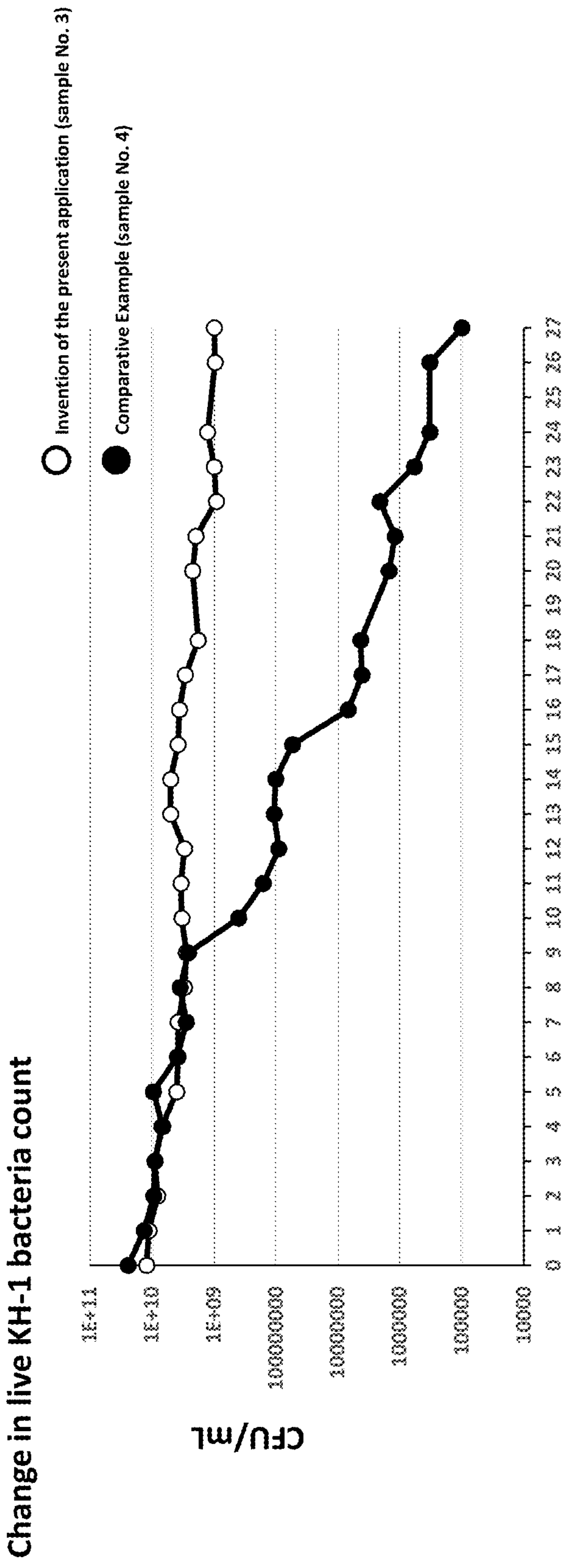
FIG. 2 is a graph showing the change in viable bacteria count in the spawn suspension of the invention (invention of the present application, sample No. 3) and a culture solution from directly storing a culture solution by omitting the harvesting step and resuspension step (Comparative Example, sample No. 4).

FIG. 2 is a graph showing the change in viable bacteria count in a spawn suspension obtained in steps 1 to 4 described above (invention of the present application, sample No. 3) and a culture solution from directly storing, in the manner of step 4, a culture solution obtained from step 1 and omitting steps 2 and 3 described above (Comparative Example, sample No. 4). As can be understood from results in FIG. 2, the viability rate can be maintained without aeration for a long period of time by undergoing steps 2 and 3 (see Example 1).

Figure 3:
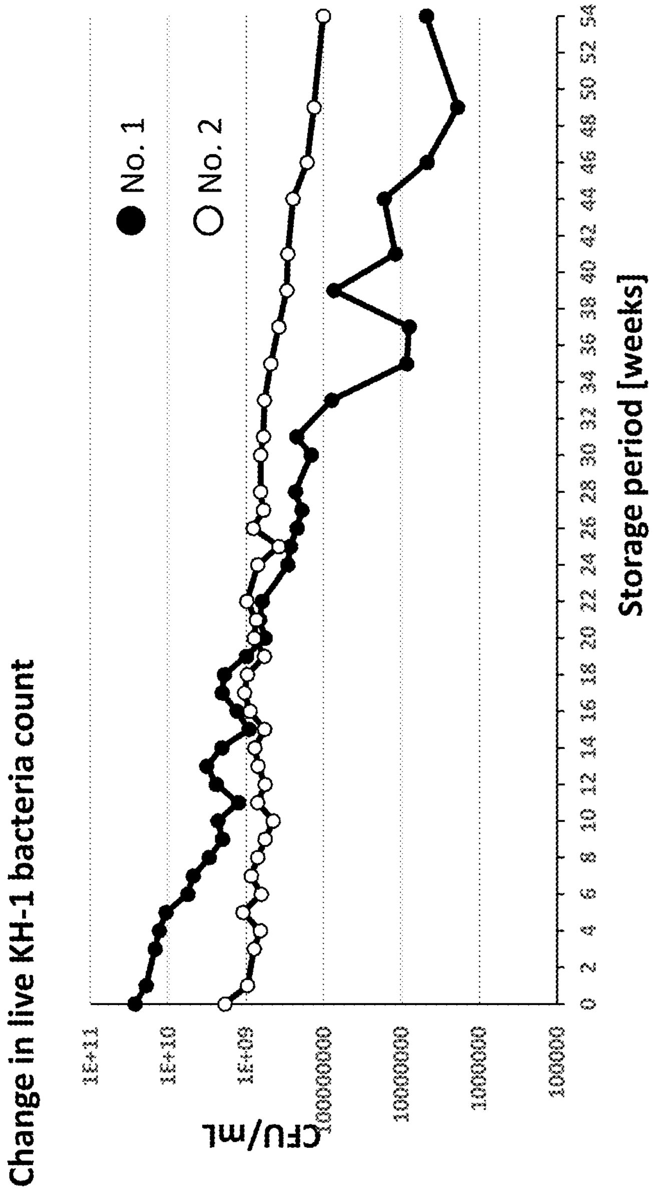
FIG. 3 is a graph showing the relationship between the initial concentration of a spawn suspension and viability rate.

As shown in the results of FIG. 3, long-term viability was higher at the order of $10^9$ cells/mL than $10^{10}$ cells/mL. Thus, in a preferred embodiment, the concentration of microorganisms in a spawn suspension can be $1\times10^8$ to $2\times10^{10}$ cells/mL, preferably $1\times10^8$ to $9\times10^9$ cells/mL, and more preferably $1\times10^8$ to $2\times10^9$ cells/mL (see Example 2).

Figure 4:
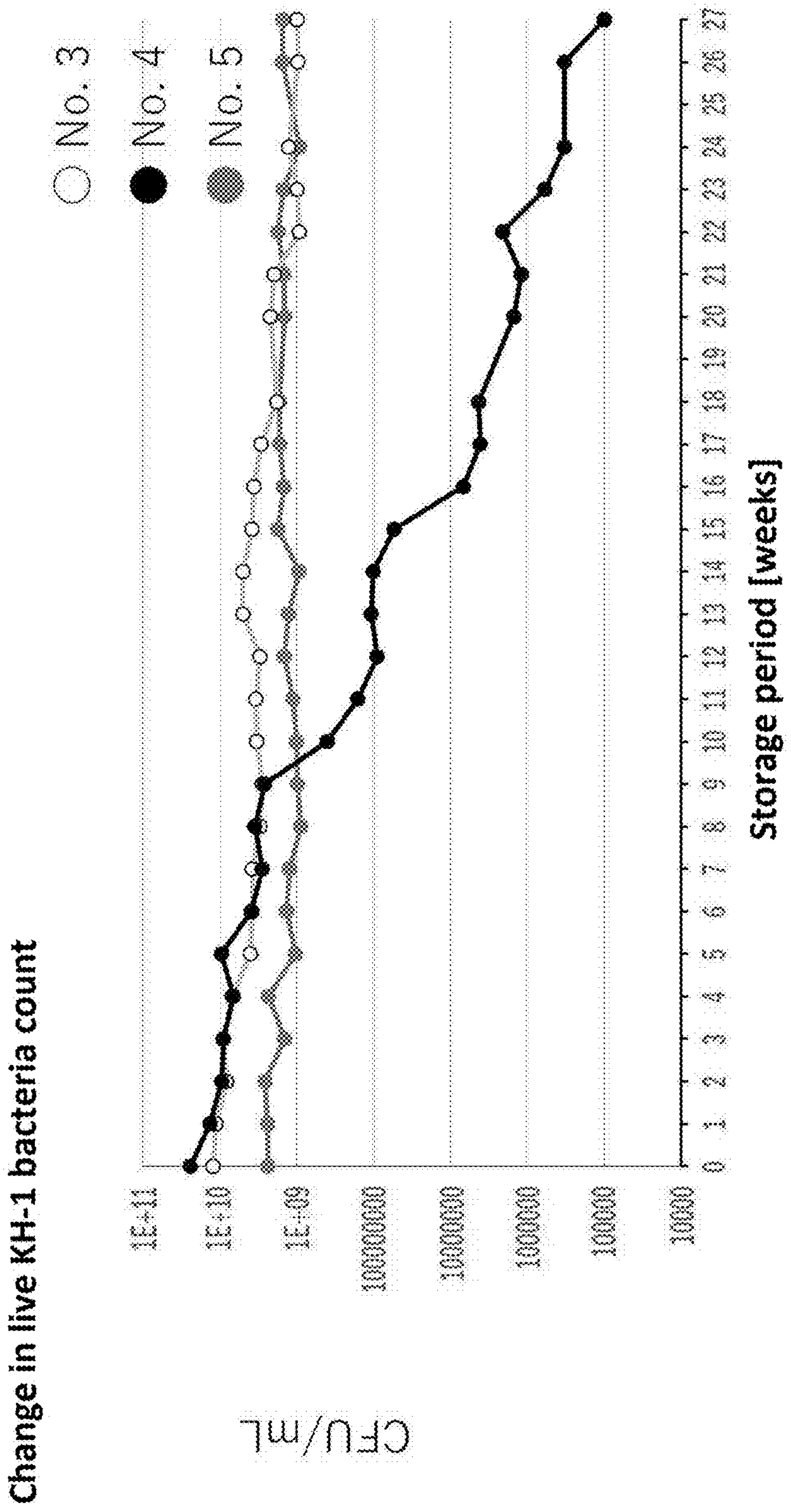
FIG. 4 is a graph showing the change in viable bacteria count for the spawn suspension of the invention obtained through harvesting and resuspension steps (sample No. 3), a culture solution from directly storing a culture solution by omitting the harvesting and resuspension steps (sample No. 4), and a culture solution stored after diluting a culture solution 10-fold with an inorganic salt medium to the order of $10^9$ cells/mL (sample No. 5).

Since a culture solution with a concentration of about $10^{10}$ cells/mL is obtained in normal batch culture, the solution may be suspended in an inorganic salt medium to dilute the solution 10-fold. FIG. 4 is a graph comparing viable bacteria preservation when a culture solution, after step 1 described above, is diluted 10-fold with an inorganic salt medium to adjust the cell concentration to the order of $10^9$ cells/mL (sample No. 5) with the viable bacteria preservation in Comparative Example 1 described above (sample No. 4). Sample No. 3 corresponds to a spawn suspension obtained through steps 1 to 4 shown in FIG. 2 (invention of the present application, sample No. 3). As can be understood from the results in FIG. 4, long-term preservation of live bacteria to the same degree as an embodiment for resuspending in an inorganic salt medium can be achieved without aeration, just by diluting 10-fold (see Example 3). Although not intended to be bound by any theory, this is understood to be due to reduced concentration of waste products in the process of dilution, and a carbon source being nearly consumed already in the culturing process, resulting in a state that is substantially free of a carbon source by dilution.

(Dry Cells)

Conventional microorganism drying methods are mainly applied to gram-positive bacteria that are resistant to drying, especially spore-forming bacteria and spore-forming yeasts. Meanwhile, many microorganisms without such formation, especially eubacteria, do not have special means for resisting drying. For example, *Burkholderia arbolis*, which is lipase secreting bacteria that consume and assimilate oil and fat and fatty acid, is gram-negative bacteria that are non-spore-forming bacteria without dry resistance. There was no efficient method of manufacturing dry cells for such gram-negative bacteria.

As a result of diligent studies, the inventor discovered that activity can be mostly maintained by subjecting microorganisms to coagulation and settling, dehydration, centrifugation, etc. to prepare wet cell clumps, suspending the clumps in water comprising whey (e.g., about 1 w/v %), and then drying the suspension under reduced pressure to dry the clumps. For example for the aforementioned *Burkholderia arbolis*, it was found that 50% or more of lipase activity, which is an indicator of oil and fat degrading capability, can be maintained relative to the activity prior to drying.

The present invention was completed after further studies based on such findings and provides the following method of manufacturing a dry microorganism formulation, a protective agent for drying microorganisms under reduced pressure, and a dry microorganism formulation.

A dry microorganism formulation obtained by the present invention maintains a significant level of enzymatic activity prior to drying. The method of manufacturing a dry microorganism formulation of the invention can alleviate reduction in enzymatic activity after drying broadly in any microorganism, but the method is also broadly applicable to and readily practiced on microorganisms other than dry resistant gram-positive bacteria and yeasts (e.g., gram-negative bacteria that are non-spore-forming bacteria).

The protective agent for drying microorganisms under reduced pressure of the invention can enhance the viability rate when drying microorganisms other than dry resistant gram-positive bacteria and yeasts (e.g., gram-negative bacteria that are non-spore-forming bacteria) under reduced pressure.

The method of manufacturing a dry microorganism formulation of the invention is characterized by comprising a step of mixing whey with microorganisms and drying the mixture under reduced pressure.

The protective agent for drying microorganisms under reduced pressure of the invention is characterized by having whey as an active ingredient.

The microorganisms described above are not particularly limited, as long as the microorganisms can be dried by the method of the invention. Various microorganisms such as bacteria, archaea, and fungi can be broadly used. One type of microorganisms alone or two or more types of microorganisms can be mixed and used.

Examples of bacteria to which the method of manufacturing a dry microorganism formulation of the invention can be applied include gram-negative bacteria (e.g., photosynthetic bacteria, cyanobacteria, bacteria of the genus *Pseudomonas*, proteobacteria, enterobacteria, chemically synthesized autotrophic bacteria, methanogenic bacteria, etc.) and gram-positive bacteria (e.g., staphylococci, spore-forming *Bacillus*, lactic acid bacteria, coryneform bacteria, *Actinomyces*, etc.). In particular, gram-negative bacteria, especially gram-negative bacteria which are non-spore-forming bacteria are suitable because said bacteria have low resistance to drying, and it is difficult to apply conventional drying methods thereon.

Examples of fungi to which the method of manufacturing a dry microorganism formulation of the invention can be applied include yeasts (e.g., yeasts of the genus *Candida*, yeast of the genus *Yarrowia*, yeast of the genus *Saccharomyces*, yeast of the genus *Schizosaccharomyces*, yeast of the genus *Pichia*, yeast of the genus *Cryptococcus*, yeast of the genus *Trichosporon*, yeast of the genus *Hansenula*, etc.), filamentous bacteria (of the genus *Aspergillus*, etc.), etc.

Examples of microorganisms used, when a dry microorganism formulation is an oil and fat degrading microorganism formulation, include lipase secreting microorganisms that consume and assimilate fatty acid described above, microorganisms that consume and assimilate glycerol, microorganisms that assimilate free fatty acid and do not secrete lipase, etc.

Specific examples of microorganisms used in the manufacture of a dry oil and fat degrading microorganism formulation include *Burkholderia arbolis, Candida cylindracea*, and *Yarrowia lipolytica*. It is desirable to combine and use two or three types thereof.

While it is known that viability rate of non-spore-forming microorganisms decreases significantly in dry storage, the inventor unexpectedly discovered that death due to drying can be prevented even in non-spore-forming microorganisms by using whey.

Microorganisms can be manufactured through culturing by a known method. After culturing, microorganisms can be harvested from a culture solution as wet cell clumps by coagulation and settling, dehydration, centrifugation, etc.

and optionally washed, etc., to obtain wet cells, and the wet cells can be used after mixing with whey.

Whey is also known as milk serum, which is a yellowish green liquid discharged after removing curd generated by adding rennet or acid to milk or skim milk. Whey is obtained as a byproduct from the manufacture of cheese or casein. Whey includes sweet whey obtained in the manufacture of cheese or rennet casein, acid whey obtained in the manufacture of acid casein, etc. Whey includes components such as proteins, lactose, water-soluble vitamin, salts (mineral components), etc. Concentrated whey, dried whey, powder whey, etc. can also be used as whey.

Since a large quantity of whey is discharged as a byproduct in the manufacture of cheese, whey is available at a low cost.

A method of mixing whey with microorganisms is not particularly limited. Various known methods can be used. Examples of methods of mixing whey with microorganisms include a method of suspending microorganisms converted into a wet cell clump in a solution comprising whey.

The amount of such whey added in a solution for suspending microorganisms is not particularly limited, as long as the effect of the present invention is attained. The amount is 0.1 w/v % or greater, preferably 0.5 w/v % or greater, more preferably 1 w/v % or greater such as 0.1 to 5 w/v %, preferably 0.1 to 3 w/v %, and more preferably 0.5 to 2 w/v %. Water can be suitably used as a solvent of a solution comprising whey.

The ratio of mixing microorganisms with whey can generally be about 1 mg to about 5 mg, preferably about 2 mg to about 3 mg of whey to $1\times10^{10}$ cells of microorganisms.

Other components besides whey and microorganisms can be optionally included in a mixture of whey and microorganisms.

Drying under reduced pressure is also known as vacuum drying, and is a method of drying under reduced pressure at or below atmospheric pressure. Unlike lyophilization, drying under reduced pressure is performed without freezing the subject to be dried. Drying under reduced pressure is generally performed at 20 to 60° C., preferably at 30 to 50° C. The subject of drying can also be heated as needed. The degree of reduced pressure can be any pressure as long as microorganisms can be dried without freezing. Reduced pressure is preferably, but not limited to, slightly reduced pressure that is somewhat lower than atmospheric pressure (e.g., 970 HPa). Drying under reduced pressure can be performed using commercially available equipment.

The manufacturing method of the invention can also perform other steps in addition to the step of drying under reduced pressure.

A dry microorganism formulation obtained by the manufacturing method of the invention can be placed in a suitable container and refrigerated or stored at ambient temperature. A desiccant, etc. can be placed in a container containing a dry microorganism formulation to maintain a dry state.

The method of manufacturing a dry microorganism formulation of the invention using whey is also broadly applicable to and readily practiced on microorganisms other than dry resistant gram-positive bacteria and yeasts (e.g., gram-negative bacteria that are non-spore-forming bacteria). A dry microorganism formulation obtained by the present invention maintains 50% or more of enzymatic activity (e.g., lipase activity in *Burkholderia arbolis*) prior to drying.

In view of drying under reduced pressure, the present invention can reduce the cost associated with transportation or storage and can be readily scaled-up.

Figure 5:
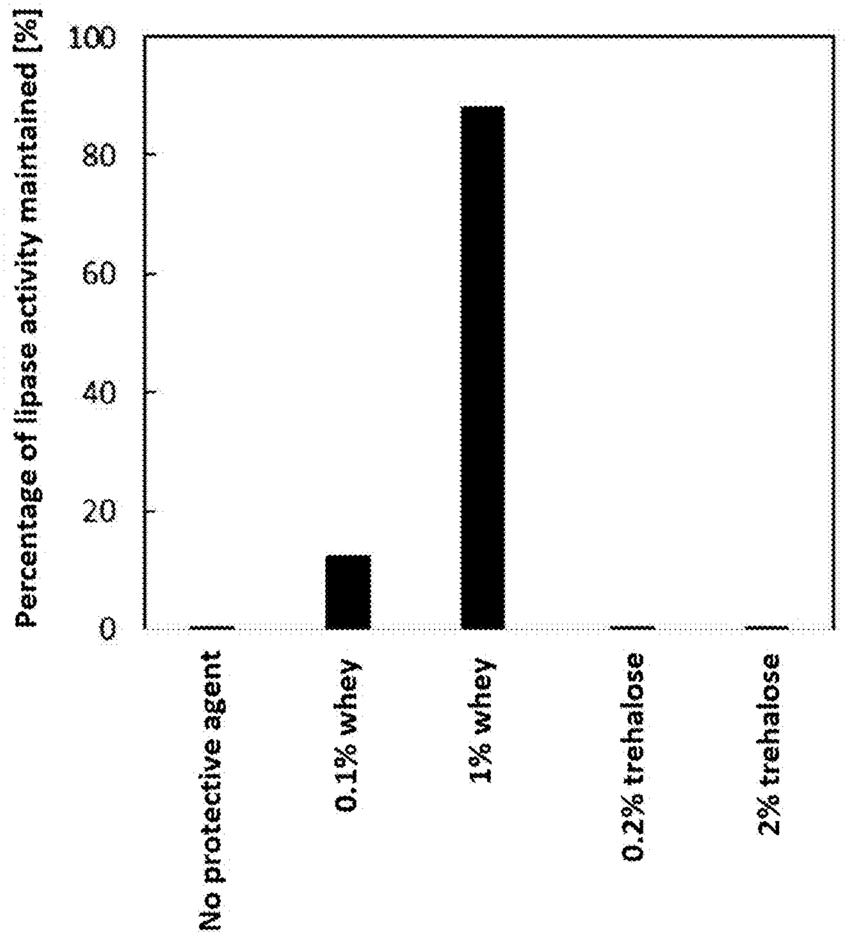
FIG. 5 is a graph showing the percentage of lipase activity maintained (%) of a formulation after drying treatment for various dry formulations obtained by drying treatments, relative to formulations before drying treatment.

As shown in FIG. 5, whey can result in maintaining the enzymatic activity of a microorganism formulation before and after drying as compared to an embodiment without a protective agent or embodiment using trehalose which is known as a protective agent. In particular, a microorganism formulation added with 1 w/v % whey and subjected to drying under reduced pressure notably maintained lipase activity as compared with before drying. In an embodiment without a protective agent or embodiment using trehalose as a protective agent, lipase activity was 20% or less as compared to before drying. An advantageous effect of a dry formulation using whey and the manufacturing method thereof of the invention is demonstrated.

In the present invention, spawns may be stored as a dry formulation described above and suspended in a liquid so that a concentration would be $1\times10^{8}$ cells/mL or greater, prior to being supplied as a spawn suspension to a thermostatic vessel, and the spawn suspension prepared in this manner may be continuously supplied to the thermostatic vessel. "In a liquid" in such a case is typically a medium or water, but can be any solution for suspending spawns, such as a buffer or salt solution.

In an embodiment of preparing a concentrated suspension from a dry cell for a moment and supplying the suspension to a thermostatic vessel or culture solution, the spawn suspension uses dry cells as a starting material, so that the concentration can be freely adjusted. For example, a spawn suspension with a high concentration of about $2\times10^{1000}$ cells/mL can also be prepared. When a spawn suspension with a concentration of about $2\times10^{1000}$ cells/mL is used, the feed flow rate or feed amount of the spawn suspension may be about 1/100 as compared to an embodiment using a spawn suspension with a common spawn suspension concentration of $1\times10^{8}$ to $2\times10^{10}$ cells/mL.

EXAMPLES

Example 1

This Example studied the effect of using *Burkholderia arbolis* KH-1 as microorganisms, removing the culture supernatant, and resuspending the microorganism cells in a fresh medium free of a carbon source, on the preservation of a spawn suspension by the change in viability rate of microorganisms.

1. Culturing step: KH-1 was batch-cultured to $1\times10^{8}$ to $2\times10^{10}$ cells/mL at 30° C. in an inorganic salt medium supplemented with canola oil (1 v/v %) as a carbon source. The composition of the inorganic salt medium was 3.5 g/L of $Na_2HPO_4$, 2.0 g/L of $KH_2PO_4$, 4 g/L of $(NH_4)_2SO_4$, 0.34 g/L of $MgCl_2\cdot6H_2O$, 2.8 mg/L of $FeSO_4\cdot7H_2O$, 2.4 mg/L of $MnSO_4\cdot5H_2O$, 2.4 mg/L of $CoCl_2\cdot6H_2O$, 1.7 mg/L of $CaCl_2\cdot2H_2O$, 0.2 mg/L of $CuCl_2\cdot2H_2O$, 0.3 mg/L of $ZnSO_4\cdot7H_2O$, and 0.25 mg/L of $NaMoO_4$.
2. Harvesting step: A culture solution obtained in the culturing step described above was centrifuged under the conditions of 2000×g, 15 min, and 4° C., and wet cell clumps were retrieved.
3. Resuspension step: The harvested wet cell clumps were resuspended in an inorganic salt medium which is not supplemented with canola oil so that the total volume would be 100 ml to prepare a spawn suspension.
4. Storing step: The spawn suspension was placed in a 100 ml medium bottle, and a lid was placed thereon to shield light for incubating and storing the suspension in a sealed state at 4° C. Aeration with a blower was not performed during storage.

As a Comparative Example, a culture solution prepared by directly storing, as in step 4, a culture solution obtained in step 1 while omitting steps 2 and 3 described above was used.

The viable microorganism count in a spawn solution in the present invention and Comparative Example was measured. The viable microorganism count was measured by appropriately diluting a spawn suspension with an inorganic salt medium, adding 100 μL of the diluent dropwise to an LB agar medium plate, culturing the microorganisms at 28° C., and counting the number of colonies. The results are shown in FIG. 2. As can be understood from the results in FIG. 2, the viability rate can be maintained for a long period of time without aeration through steps 2 and 3.

Example 2

Subsequently, the relationship between the viability rate and the initial concentration of the spawn suspension obtained in Example 1 was studied. The results are shown in FIG. 3. As can be understood from the results in FIG. 3, long term viability was higher at the order of $10^9$ cells/mL than at the order of $10^{10}$ cells/mL.

Example 3

The viable microorganism count was measured for a culture solution, which is, after step 1 in Example 1, diluted 10-fold with an inorganic salt medium to the order of $10^9$ cells/mL and then stored as in step 4 (sample No. 5 in FIG. 4) and a culture solution stored directly without dilution. Sample No. 3 in FIG. 4 corresponds to the spawn suspension shown in FIG. 2 (invention of the present application, sample No. 3).

As can be understood from the results in FIG. 4, the viability rate was able to be maintained for a long period of time without aeration in the same manner as an embodiment of resuspending microorganisms in an inorganic salt medium by diluting the solution 10-fold.

Example 4

3 mL of culture solution comprising *Burkholderia arbolis* SL1B1 at $2\times10^9$ cells/mL and *Yarrowia lipolytica* 1A1 at $3\times10^7$ cells/mL was subjected to centrifugation, and the resulting wet cell clumps were resuspended in 0.1 mL of water without a protective agent or an aqueous whey solution (0.1 w/v % or 1 w/v %) or aqueous trehalose solution (0.2 w/v % or 2 w/v %). The suspensions were centrifuged and dried under reduced pressure at 28° C. and 550 rpm for 2.5 hours (TOKYO RIKAKIKAI UT-200). The resulting dry microorganisms refrigerated overnight at 4° C. were used as the spawns of the culture described below.

A formulation prior to being dried and a formulation that has been dried containing equal amounts of cells were each added to a 500 mL Erlenmeyer flask with a baffle comprising 100 mL of an inorganic salt medium supplemented with canola oil (3 v/v %) and cultured for 24 hours to calculate the ratio of lipase activity maintained (%) of a formulation that has been dried to that of a formulation prior to being dried. Lipase activity was measured by a lipase assay described below.

A substrate solution for a lipase assay was prepared by mixing 18.9 mg of 4-nitrophenyl palmitate (4-NPP) with 12 ml of 3 v/v % triton-X at 70° C. A mixture of 1 ml of the substrate solution, 0.9 ml of deionized water, and 1 ml of 150 mM GTA buffer (a solution consisting of 150 mM of 3,3-dimethylglutaric acid, 150 mM Tris, and 150 mM of 2-amino-2-methyl-1,3-propanediol adjusted to a pH of 6 with NaOH or HCl) was pre-incubated at 28° C. in a quartz cell. An enzymatic reaction was initiated by adding 100 μl of culture supernatant after 24 hours of culture described above. The lipase activity was found by monitoring absorbance at 410 nm by using a U-2810 spectrophotometer comprising a temperature controlled cell holder (Hitachi, Tokyo, Japan). Enzymatic activity resulting in 1 μmol of 4-nitrophenol in one minute was considered as 1 unit of lipase activity. The ratio of activity maintained between a formulation prior to being dried and a formulation that has been dried was calculated.

The results are shown in FIG. 5. It can be understood from FIG. 5 that whey results in a significantly higher effect of maintaining enzymatic activity before and after drying as compared with an embodiment without a protective agent or an embodiment using trehalose, which is known as a protective agent. In particular, a microorganism formulation added with 1% whey and dried under reduced pressure maintained 80% or more lipase activity as compared to before drying. The lipase activity was 5% or less as compared to before drying in an embodiment without a protective agent or an embodiment using trehalose as a protective agent. An advantageous effect of a dry formulation using whey and a manufacturing method thereof of the invention was demonstrated.

Example 5

This Example shows that the growth of microorganisms is suppressed even for a carbon source or nitrogen source with which microorganisms can grow at a low concentration if a high concentration aqueous solution that does not comprise other components required for growth is prepared. An aqueous ammonium sulfate solution comprising ammonium sulfate with a final concentration of 20% as a nitrogen source in ultrapure water (concentrated nitrogen source), and an aqueous solution from mixing ethanol with a final concentration of 50 v/v % and 5 w/v % glucose as carbon sources in ultrapure water (concentrated carbon source) were prepared. A medium from mixing 2 v/v % ethanol and 0.2 w/v % glucose in an inorganic salt BS medium was also prepared (Comparative Example). These aqueous solutions and medium were subjected to an experiment without sterilization. 5 mL of aqueous concentrated carbon source solution or medium in a 50 mL tube was inoculated with 1/100 amount of *E. coli* BL21 strain precultured in an LB medium, and incubated while shaking for 3 days at 28° C. Inoculation used bacteria that were cultured in an LB liquid medium, then harvested by centrifugation, washed twice with ultrapure water, then resuspended in ultrapure water to achieve turbidity of OD=about 1.8. An inorganic salt BS medium with the composition in the following table was used.

TABLE 1

| BS medium composition | *free of Yeast Extract |
|---|---|
| $Na_2HPO_4$ | 4.9 g |
| $KH_2HPO_4$ | 2 g |
| $NH_4(SO_4)_2$ | 2 g |
| M.E. solution | 1 mL |

TABLE 1-continued

| BS medium composition | *free of Yeast Extract |
|---|---|
| $MgCl_2 \cdot 6H_2O$ (340 g/L) | 1 mL |
| Up to | 1 L |

Figure 6:
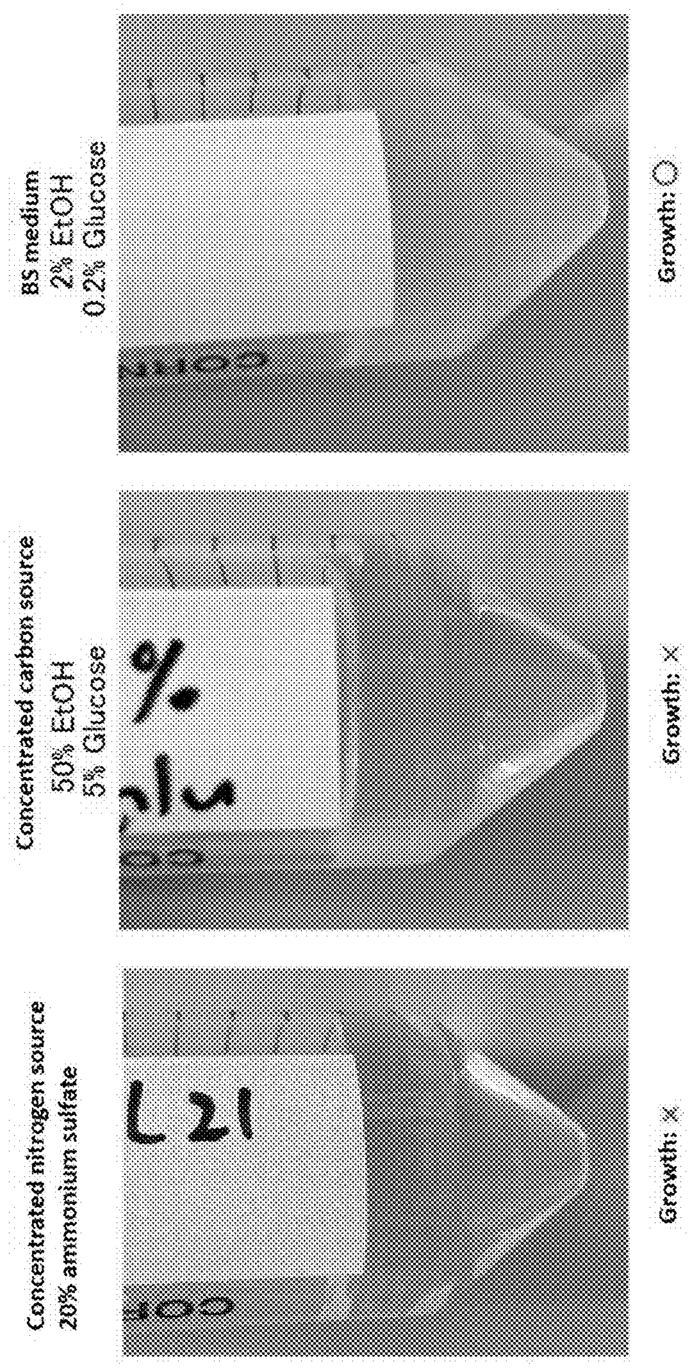
FIG. 6 shows the results of growing *E. coli* in an aqueous solution prepared by dissolving 20% ammonium sulfate as a nitrogen source in pure water, an aqueous solution prepared by mixing and dissolving ethanol with a final concentration of 50 v/v % and glucose of 5 w/v % as a carbon source in pure water, or a medium prepared by mixing ethanol with a final concentration of 2 v/v % and glucose of 0.2 w/v % as a carbon source in an inorganic salt BS medium.

As shown in FIG. 6, growth of microorganisms was confirmed under the conditions of the Comparative Example, but microorganisms could not grow in the aqueous concentrated nitrogen source solution or the aqueous concentrated carbon source solution. Accordingly, it was demonstrated that even microorganisms that can grow in a medium comprising a carbon source, a nitrogen source, and other required medium components at a suitable concentration cannot grow in a concentrated partial medium comprising only a nitrogen source or a carbon source. It was revealed that such a concentrated partial medium does not need to be sterilized.

Various embodiments described above can be combined to provide additional embodiments. Those skilled in the art can make any suitable modification to the embodiments in light of the above detailed descriptions. In general, the terms used in the appended claims should not be interpreted to limit the claims to the specific embodiments disclosed in the specification, but should be interpreted to encompass the entire scope of any possible embodiment and equivalent embodiments of such claims to which a right is granted. Thus, the claims are not limited by the present disclosure.

INDUSTRIAL APPLICABILITY

The present invention provides a method of efficiently and continuously manufacturing microorganisms while economizing the amount of microorganisms used as spawns and a system therefor.

In particular, the present invention provides a novel continuous microorganism manufacturing method and system with less need for sterilization to avoid germ contamination as compared to common methods and systems for growing microorganisms.

Interest in microorganism catalysts has increased recently. Development of an efficient method of growing microorganisms is a pressing problem to be solved. The present invention solves such a problem by providing a novel continuous microorganism manufacturing method and/or a system therefor.

The invention claimed is:

1. A method of continuously manufacturing microorganisms, comprising:

continuously supplying, for 20 hours or longer, a first concentrated partial medium from a first medium storage vessel at constant flow rate Y1 (L/h), a second concentrated partial medium from a second medium storage vessel which is different from the first medium storage vessel at flow rate Q (L/h), and water at constant flow rate Y2 (L/h), each independently to a thermostatic vessel, or to the thermostatic vessel after mixing in a mixing vessel or a supply line, to form a medium required for the microorganisms;

growing microorganisms that can assimilate a carbon source and grow in a culture solution in the thermostatic vessel by aerating the thermostatic vessel to continuously manufacture a microorganism culture solution for 20 hours or longer; and continuously discharging the microorganism culture solution comprising a substantially constant concentration of microorganisms from the thermostatic vessel at constant flow rate F (L/h) for 20 hours or longer;

characterized in that the medium required for the microorganisms is formed by a first medium component contained in the first concentrated partial medium, a second medium component contained in the second concentrated partial medium, and water, wherein the first concentrated partial medium comprises a carbon source, and the second concentrated partial medium comprises a nitrogen source.

2. The method of claim 1, characterized in that volume F (L) of the microorganism culture solution discharged each hour from the thermostatic vessel is a volume that is 1/30 to 1/2 of volume V (L) of a culture solution in the thermostatic vessel.

3. The method of claim 1, characterized in that the first concentrated partial medium or the second concentrated partial medium comprises a carbon source, and the concentrated partial medium comprising the carbon source is supplied to the thermostatic vessel so that a carbon source concentration of a culture solution in the thermostatic vessel would always be about 0.01 w/v % or less.

4. The method of claim 1, characterized in that a flow rate of a fluid supplied to the thermostatic vessel other than the second concentrated partial medium is equal to a flow rate of the culture solution discharged from the thermostatic vessel.

5. The method of claim 1, characterized in that a suspension of seeds of microorganisms is continuously supplied to the thermostatic vessel at constant flow rate X (L/h) for 20 hours or longer.

6. The method of claim 1, wherein the first concentrated partial medium does not comprise a nitrogen source, and the second concentrated partial medium does not comprise a carbon source.

7. The method of claim 6, wherein the nitrogen source is at a concentration of 10 w/v % or greater.

8. The method of claim 6, wherein the carbon source is at a concentration of 40 w/v % or greater.

9. The method of claim 1, characterized in that:

1) The first concentrated partial medium, the second concentrated partial medium, and water used in the continuous manufacture are not sterilized; or 2) The first medium storage vessel, the second medium storage vessel, and the thermostatic vessel are not sterilized within 24 hours before and after the continuous manufacture of 20 hours or longer.

10. The method of claim 9, characterized in that the first medium storage vessel, the second medium storage vessel, and the thermostatic vessel are not sterilized within 72 hours before and after the continuous manufacture of 20 hours or longer.

11. The method of claim 1, characterized in that the thermostatic vessel is operated so that a temperature of a culture solution in the thermostatic vessel would be 18 to 55° C., a dissolved oxygen concentration would be 0.1 mg/L or greater, and a pH would be 6.0 to 8.0.

12. The method of claim 1, characterized in that a culture solution discharged from the thermostatic vessel comprises the microorganisms at $1\times10^9$ cells/mL or greater.

13. The method of claim 1, characterized in that the microorganisms comprise at least one type selected from the group consisting of bacteria and yeasts.

14. The method of claim 1, characterized in that the microorganisms comprise at least one type selected from the group consisting of gram-negative bacteria and yeasts.

15. The method of claim 5, characterized in that the seeds are prepared by removing culture supernatant from the microorganisms that have been batch-cultured, resuspending the microorganisms in a fluid free of a carbon source so that a concentration would be $1\times10^8$ to $2\times10^{10}$ cells/mL, and refrigerating the microorganisms.

16. The method of claim 5, characterized in that the seeds are prepared by diluting the microorganisms that have been batch-cultured 10-fold with a fluid free of a carbon source so that a concentration would be $1\times10^8$ to $2\times10^{10}$ cells/mL, and then refrigerating the microorganisms.

17. The method of claim 5, characterized in that the seeds are stored as dry cells of the microorganisms and suspended in a liquid so that a concentration would be $1\times10^8$ cells/mL or greater prior to being supplied to the thermostatic vessel as a seed suspension, and a seed suspension prepared in this manner is supplied to the thermostatic vessel.

18. The method of claim 1, characterized in that seeds of the microorganisms stored as dry cells are directly supplied to the thermostatic vessel.

19. The method of claim 17, wherein the dry cells are stored without refrigerating.

20. The method of claim 18, wherein the dry cells are stored without refrigerating.

* * * * *